United States Patent
Liu

(10) Patent No.: US 11,090,511 B2
(45) Date of Patent: Aug. 17, 2021

(54) MOTION MANAGEMENT SYSTEM AND METHOD FOR IMAGE-GUIDED RADIOTHERAPY

(71) Applicant: Medical Intelligence Medizintechnik GmbH, Schwabmunchen (DE)

(72) Inventor: Rui Liu, Augsburg (DE)

(73) Assignee: MEDICAL INTELLIGENCE MEDIZINTECHNIK GMBH

(*) Notice: Subject to any disclaimer, the term of this patent is extended or adjusted under 35 U.S.C. 154(b) by 0 days.

(21) Appl. No.: 16/647,772

(22) PCT Filed: Sep. 18, 2018

(86) PCT No.: PCT/EP2018/075246
§ 371 (c)(1),
(2) Date: Mar. 16, 2020

(87) PCT Pub. No.: WO2019/053293
PCT Pub. Date: Mar. 21, 2019

(65) Prior Publication Data
US 2020/0230439 A1  Jul. 23, 2020

(30) Foreign Application Priority Data
Sep. 18, 2017 (EP) .................................... 17191708

(51) Int. Cl.
*A61N 5/10* (2006.01)
*A61M 16/00* (2006.01)
(Continued)

(52) U.S. Cl.
CPC .......... *A61N 5/1068* (2013.01); *A61B 5/0036* (2018.08); *A61B 5/055* (2013.01);
(Continued)

(58) Field of Classification Search
CPC .. A61N 5/1064; A61N 5/1065; A61N 5/1067; A61N 5/1068
See application file for complete search history.

(56) References Cited

U.S. PATENT DOCUMENTS

| 6,597,939 | B1* | 7/2003 | Lampotang | A61B 6/541 128/202.13 |
| 2012/0083645 | A1* | 4/2012 | Sun | A61N 5/1068 600/1 |

(Continued)

FOREIGN PATENT DOCUMENTS

| GB | 2107553 A | 4/1983 |
| GB | 2527538 A | 12/2015 |

(Continued)

OTHER PUBLICATIONS

"International Application Serial No. PCT EP2018 075246, International Preliminary Report on Patentability dated Mar. 24, 2020", (Mar. 24, 2020), 8 pgs.

(Continued)

*Primary Examiner* — Carrie R Dorna
(74) *Attorney, Agent, or Firm* — Quarles & Brady LLP

(57) ABSTRACT

Systems for establishing a reproducible breath-holding pattern during radiotherapy are disclosed. An exemplary image-guided radiotherapy system (100) may include an airway breathing controller (ABC) device (160), which may block airflow to the patient during imaging and/or radiotherapy to immobilize a target tumor. A patient may practice breath-holding during a training session until a reproducible breath-hold pattern is established. The patient may perform the breath-hold pattern in imaging and/or radiotherapy sessions, during which physiological signals may be measured from the patient and compared to baseline signals collected during the training session. Variation between measured signals and (Continued)

baseline signals may indicate unreproducible breath-holding, in which case radiation delivery may be altered or halted.

10 Claims, 10 Drawing Sheets

(51) Int. Cl.
*A61B 5/00* (2006.01)
*A61B 5/055* (2006.01)

(52) U.S. Cl.
CPC ......... *A61M 16/024* (2017.08); *A61N 5/1037* (2013.01); *A61M 2230/04* (2013.01); *A61M 2230/40* (2013.01); *A61N 2005/1055* (2013.01)

(56) References Cited

U.S. PATENT DOCUMENTS

| | | | |
|---|---|---|---|
| 2013/0116555 A1* | 5/2013 | Kuzelka | A61M 16/024 600/427 |
| 2016/0074674 A1* | 3/2016 | Kohli | A61B 5/0205 600/484 |

FOREIGN PATENT DOCUMENTS

| | | |
|---|---|---|
| WO | WO-9816151 A1 | 4/1998 |
| WO | WO-9852635 A1 | 11/1998 |
| WO | WO-2012044715 A1 | 4/2012 |
| WO | WO-2019053293 A1 | 3/2019 |

OTHER PUBLICATIONS

"European Application Serial No. 17191708.1, Extended European Search Report dated Mar. 2, 2018", 5 pgs.

"European Application Serial No. 17191708.1, Response filed Sep. 20, 2019 to Extended European Search Report dated Mar. 2, 2018", 18 pgs.

"International Application Serial No. PCT/EP2018/075246, International Search Report dated Dec. 6, 2018", 5 pgs.

"International Application Serial No. PCT/EP2018/075246, Written Opinion dated Dec. 6, 2018", 6 pgs.

Johannes, F.T. Arnold, et al., "Lung MRI using an MR-compatible active breathing control (MR-ABC)", Magnetic Resonance in Medicine, vol. 58, No. 6, (Jan. 1, 2007), 1092-1098 pgs.

\* cited by examiner

MOTION MANAGEMENT SYSTEM AND METHOD FOR IMAGE-GUIDED RADIOTHERAPY

PRIORITY APPLICATIONS

This application is a U.S. National Stage Filing under 35 U.S.C. 371 from International Application No. PCT/EP2018/075246, filed on Sep. 18, 2018, and published as WO2019/053293 on Mar. 21, 2019, which claims the benefit of priority to European Application No. 17191708.1, filed on Sep. 18, 2017; the benefit of priority of each of which is hereby claimed herein, and which applications and publication are hereby incorporated herein by reference in their entirety.

TECHNICAL FIELD

This disclosure relates generally to radiation therapy or radiotherapy. More specifically, this disclosure relates to systems and methods for managing patient motion in image-guided radiotherapy.

BACKGROUND

Radiotherapy is used to treat cancers and other ailments in mammalian (e.g., human and animal) tissue. Radiotherapy is often provided using a linear accelerator (LINAC), whereby a target site such as a tumor is irradiated by high-energy particles (e.g., electrons, protons, ions and the like). During the course of radiotherapy, images of the target tumor and surrounding tissues may be acquired using an imaging device to improve placement and dosage of the radiation beam. For example, information revealed by the images may be used to compensate for changes in tumor size or position, and for movement of the patient.

During treatment of the thoracic and upper abdominal regions, ventilation to the patient is periodically suspended to prevent movement of respiratory organs. For example, an active breathing control (ABC) device or deep inspiration breath-hold (DIBH) device may be used, which includes a mouth piece and an airflow valve which is periodically closed at a certain point in the patient's respiratory cycle to prevent airflow to and from the patient. With airflow blocked, the lungs and diaphragm may be immobilized, as are tumors or other treatment sites in proximity to the respiratory anatomy. The target tumor may then be irradiated while it is immobilized during the breath-hold, after which the airflow valve may be opened and respiration resumes.

According to these breath-holding techniques, it may be imperative that the patient sustain a reproducible breath-hold pattern during the entire treatment session, holding their breath for the same duration and at the same lung volume for each breath-hold. However, many patients struggle to maintain a reproducible breath-hold. For example, patients who are unfamiliar or uncomfortable with breath-holding may become anxious or breathless during radiotherapy, and their breathing may become faster and more shallow. Consequentially, radiotherapy sessions are often prolonged because time must be provided to allow the patient to become calm enough to resume breath-holding. Additionally, patients performing unreproducible breath-holding, such as due to panic and anxiety, often breathe in quick, unexpected movements. As a result, the radiation beam from the radiotherapy device may not be accurately aimed at the target tumor and surrounding, healthy tissue may be unintentionally irradiated.

Thus, there remains a need for training patients to obtain and maintain reproducible breath-hold patterns during radiotherapy. Additionally, there remains a need for techniques to monitor patients' respiration to ensure reproducibility in the breath-hold pattern. The present disclosure provides systems and methods for developing and maintaining a reproducible, consistent breath-hold pattern during medical imaging and radiotherapy, and for monitoring patients to ensure that reproducibility in the breath-hold pattern is maintained.

SUMMARY

Disclosed herein are systems and methods for training a patient to develop and maintain a reproducible breath-hold pattern, and for monitoring physiological signals of the patient to ensure that reproducibility in the breath-hold pattern is maintained during medical imaging and radiotherapy. Particular examples of the disclosure may enable more reproducible and consistent breath-holding, thus providing more accurate imaging of target anatomy and more precise delivery of radiation thereto.

According to an aspect of the present disclosure, a computer-implemented method for use in a radiotherapy device that emits a radiation beam to treat a target tumor of a patient is provided, wherein the radiotherapy device is used with a breath control device used to control breathing by the patient during radiotherapy. The method includes obtaining a pre-determined breath-hold pattern for the breath control device. The breath-hold pattern includes at least one ventilation suspension parameter for the breath control device, a baseline respiration signal corresponding to the at least one ventilation suspension parameter, and a baseline cardiovascular signal corresponding to the at least one ventilation suspension parameter. The method further includes detecting a respiration signal reflecting respiration of the patient and detecting a cardiovascular signal reflecting cardiovascular activity of the patient. The method further includes transmitting ventilation suspension signals to the breath control device to control the breath control device to block airflow to the patient during corresponding breath-hold periods. The ventilation suspension signals are based upon the at least one ventilation suspension parameter. The method further includes calculating a variation between the detected respiration and cardiovascular signals and the obtained baseline respiration and cardiovascular signals. The method further includes determining, when the calculated variation is below a pre-determined threshold, to gate the radiotherapy device, such that the radiotherapy device is gated to emit the radiation beam during one or more breath-hold periods and when the calculated variation is below the pre-determined threshold.

The at least one ventilation suspension parameter may be obtained during a training period and includes a breath-hold period duration and a start time of the breath-hold period. The start time may be one or more of an end-exhalation and an end-inhalation. The radiotherapy device may emit the radiation beam according to a treatment plan corresponding to the at least one ventilation suspension parameter, the baseline respiration signal, and the baseline cardiovascular signal. The cardiovascular signal may be one or more of an ECG signal and a pulse oximetry signal. The calculated variation may reflect one or more parameters associated with at least one of inhalation rising time, exhalation falling time, breath-hold period duration, respiration cycle duration, respiration signal amplitude, cardiovascular cycle duration, and cardiovascular signal amplitude. The method may further include determining, from the detected cardiovascular signal, a cardiovascular cycle duration representing a time period between two consecutive heartbeats. The calculated variation reflects a comparison between the detected respiration signal and the cardiovascular cycle duration. The method may further include evaluating the detected respiration and cardiovascular signals to predict one or more of location and movement of the target tumor. The method may further include halting emission of the radiation beam when the calculated variation is equal to or greater than the pre-determined threshold. The method may further include: determining a plurality of diastole time periods based on the detected cardiovascular signal; and determining a plurality of radiotherapy activation periods based on the occurrence of both one of the breath-hold periods and one of the diastole time periods. Gating the radiotherapy device may further include gating the radiotherapy device such that the radiotherapy device emits the radiation beam only during one or more of the plurality of radiotherapy activation periods.

According to another aspect of the present disclosure there is provided a processor-readable medium comprising instructions that, when executed by a controller of a radiotherapy device, cause the radiotherapy device to perform a method as disclosed herein.

According to another aspect of the present disclosure, a radiotherapy device for emitting a radiation beam to treat a target tumor of a patient is provided, wherein the radiotherapy device is configured to communicate with a breath control device used to control breathing by the patient during radiotherapy of the target tumor. The radiotherapy device includes a radiation beam generator and a controller. The radiation beam generator is configured to emit the radiation beam toward the target tumor according to one or more control parameters. The controller is configured to obtain a pre-determined breath-hold pattern for the breath control device. The breath-hold pattern includes at least one ventilation suspension parameter for the breath control device, a baseline respiration signal corresponding to the at least one ventilation suspension parameter, and a baseline cardiovascular signal corresponding to the at least one ventilation suspension parameter. The controller is further configured to detect a respiration signal reflecting respiration of the patient and detect a cardiovascular signal reflecting cardiovascular activity of the patient. The controller is further configured to transmit ventilation suspension signals to the breath control device to control the breath control device to block airflow to the patient during corresponding breath-hold periods. The ventilation suspension signals are based upon the at least one ventilation suspension parameter. The controller is further configured to calculate a variation between the detected respiration and cardiovascular signals and the obtained baseline respiration and cardiovascular signals. The controller is further configured to determine, when the calculated variation is below a pre-determined threshold, to gate the radiation beam generator, such that the radiation beam generator is gated to emit the radiation beam during one or more breath-hold periods and when the calculated variation is below the pre-determined threshold.

The at least one ventilation suspension parameter may be obtained during a training period and includes a breath-hold period duration and a start time of each breath-hold period. The start time may be one or more of an end-exhalation and an end-inhalation. The radiation beam generator may be configured to emit the radiation beam according to a treatment plan corresponding to the at least one ventilation suspension parameter, the baseline respiration signal, and the baseline cardiovascular signal. The cardiovascular signal may be one or more of an ECG signal and a pulse oximetry signal. The calculated variation may reflect one or more parameters associated with at least one of inhalation rising time, exhalation falling time, breath-hold period duration, respiration cycle duration, respiration signal amplitude, cardiovascular cycle duration, and cardiovascular signal amplitude. The controller may be further configured to determine, from the detected cardiovascular signal, a cardiovascular cycle duration representing a time period between two consecutive heartbeats. The calculated variation may reflect a comparison between the detected respiration signal and the cardiovascular cycle duration. The controller may be further configured to predict one or more of location and movement of the target tumor based upon the detected signals.

According to a further aspect of the present disclosure, a radiotherapy system is provided. The radiotherapy system includes a radiotherapy device comprising a radiation beam generator configured to emit a radiation beam toward a target tumor of a patient, a breath control device configured to control breathing by the patient during radiotherapy of the target tumor, a respiration sensor configured to detect a signal reflecting respiration of the patient, a cardiovascular sensor configured to detect a signal reflecting cardiovascular activity of the patient, and a controller. The controller is configured to obtain a pre-determined breath-hold pattern for the breath control device. The breath-hold pattern includes at least one ventilation suspension parameter for the breath control device, a baseline respiration signal corresponding to the at least one ventilation suspension parameter, and a baseline cardiovascular signal corresponding to the at least one ventilation suspension parameter. The controller is further configured to receive a respiration signal from the respiration sensor and receive a cardiovascular signal from the cardiovascular sensor. The controller is further configured to transmit ventilation suspension signals to the breath control device to control the breath control device to block airflow to the patient during corresponding breath-hold periods. The ventilation suspension signals are based upon the at least one ventilation suspension parameter. The controller is further configured to calculate a variation between the received respiration and cardiovascular signals and the obtained baseline respiration and cardiovascular signals. The controller is further configured to determine, when the calculated variation is below a pre-determined threshold, to gate the radiation beam generator, such that the radiation beam generator is gated to emit the radiation beam only during one or more breath-hold periods and when the calculated variation is below the pre-determined threshold.

The radiation beam generator is configured to emit the radiation beam according to a treatment plan corresponding to the at least one ventilation suspension parameter, the baseline respiration signal, and the baseline cardiovascular signal. The system may additionally include an MR imaging device configured to acquire MR image data of the target tumor. The controller may be additionally configured to receive imaging data from the imaging device; determine, from the imaging data, one or more of movement and a size change of the target tumor; and modify the treatment plan according to the one or more of determined movement and size change of the target tumor.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Exemplary embodiments generally relate to techniques for managing breath-hold patterns during medical imaging and/or radiotherapy. This may be achieved during a training session in which the system allows a patient to select a breath-hold pattern and practice the pattern's execution with an ABC device until the patient is able to comfortably and reproducibly perform the pattern. Additionally, exemplary embodiments generally relate to systems and methods for evaluating the reproducibility of the patient's breath-holding during an imaging and/or radiotherapy session. Respiration-dependent physiological signals may be collected from the patient during a session and compared to signals measured during the training session. Differences between the signals may indicate unreproducible breath-holding, and the session may be altered or halted until reproducible breath-holding is resumed.

Figure 1A:
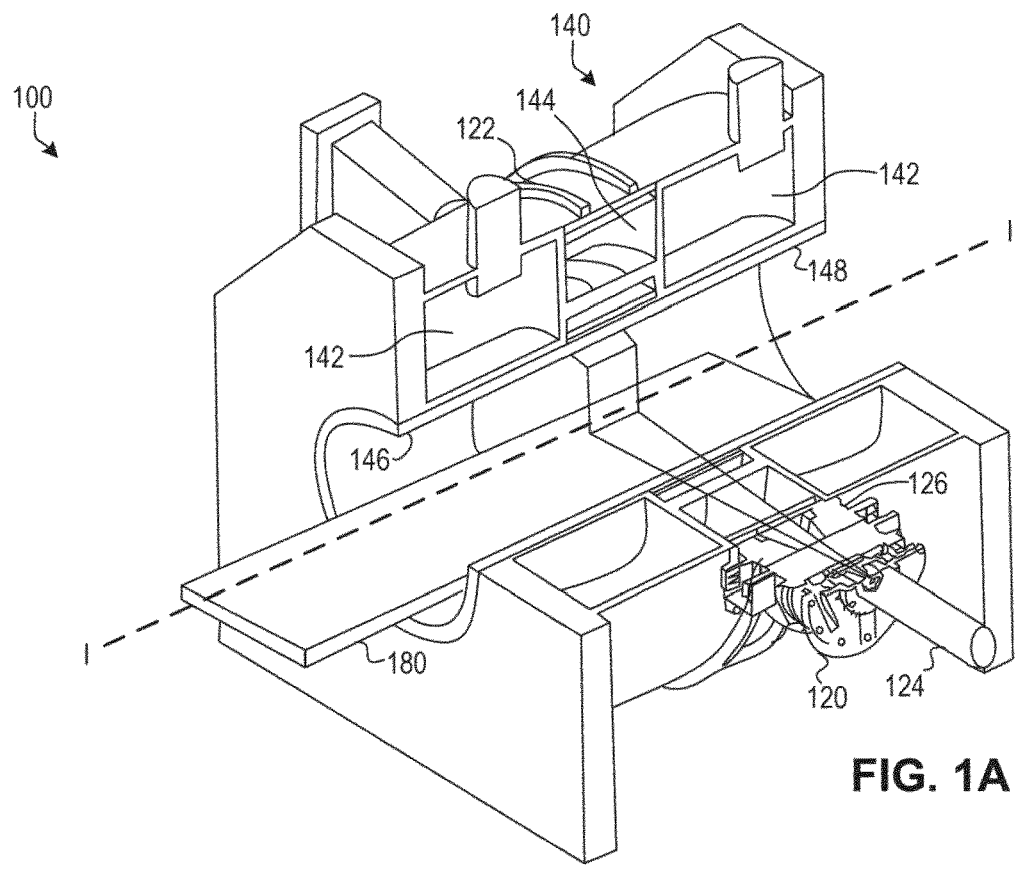
FIGS. 1A, 1B, and 2 illustrate an exemplary system for image-guided radiotherapy, according to various embodiments of the present disclosure.
Figure 1B:
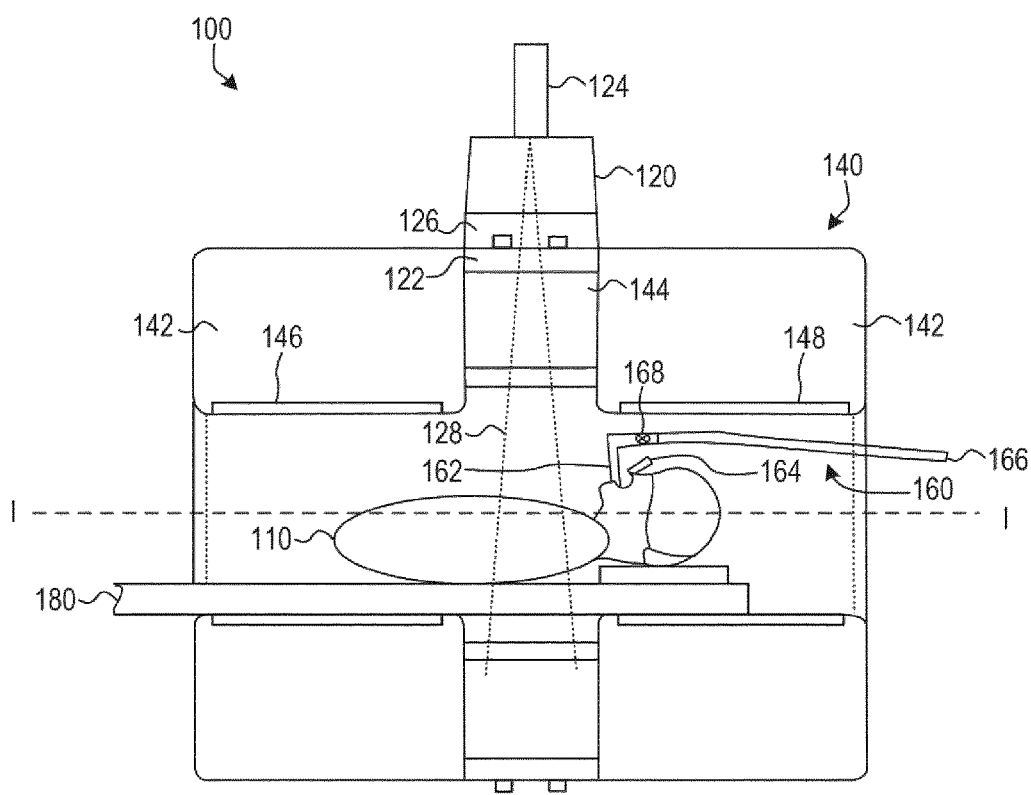

FIG. 1A and FIG. 1B illustrate views of an exemplary system 100 for image-guided radiotherapy. System 100 may include radiotherapy device 120 and medical imaging device 140. System 100 may be a combination magnetic resonance imaging (MRI) and linear accelerator system, known as an MR-LINAC. Accordingly, radiotherapy device 120 may be a LINAC device, and medical imaging device 140 may be an MRI device. However, it will be appreciated that system 100 in the present disclosure is not limited to a MR-LINAC, and that the system and devices disclosed herein may be used to enable any suitable medical imaging device, any suitable radiotherapy device, or any suitable combination medical imaging and radiotherapy device.

System 100 may include couch 180 for supporting the patient 110 in a bore or opening of system 100. Couch 180 may be movable along a horizontal, translation axis (labelled "I"), such that patient 110 may be moved into or out of the opening of system 100. In some embodiments, couch 180 may be rotatable around a central vertical axis of rotation, transverse to the translation axis. Couch 180 may form a cantilever section that projects away from a support structure (not depicted in FIGS. 1A and 1B) of the couch or of system 100. In various embodiments, couch 180 may be moved along the translation axis relative to the support structure in order to form the cantilever section, i.e. the cantilever section increases in length as couch 180 is moved and the support structure remains stationary. In alternative embodiments, both the support structure and couch 180 move along the translation axis, such that the cantilever section remains substantially constant in length, as described in the patent application published as WO 2009/007737, the contents of which are incorporated by reference and to which the skilled person is referred for a full understanding of the described embodiment.

System 100 may additionally include medical imaging device 140, which may be configured to produce real-time imaging of a patient positioned on couch 180. Medical imaging device 140 may include a primary magnet 142 which may act to generate the primary magnetic field for magnetic resonance imaging. Primary magnet 142 may consist of one or more coils with an axis that runs parallel to the translation axis I. The one or more coils may be a single coil or a plurality of coaxial coils of different diameter. In some embodiments, the one or more coils in primary magnet 142 are spaced such that a central window 144 of the magnet 142 is free of coils. In other embodiments, the coils in magnet 142 may simply be thin enough or of a reduced density such that they are substantially transparent to radiation of the wavelength generated by radiotherapy device

120. Magnet 142 may further include one or more active shielding coils, which may generate a magnetic field outside magnet 142 of approximately equal magnitude and opposite polarity to the external primary magnetic field. Portions of radiotherapy device 120, such as accelerator 124, may be positioned outside magnet 142 so as to prevent interference therebetween.

Medical imaging device 140 may further include two gradient coils 146, 148, which may generate a gradient magnetic field that is superposed on the primary magnetic field. Coils 146, 148 may generate a gradient in the resultant magnetic field that allows spatial encoding of the protons so that their position can be determined, for example coils 146, 148 may be controlled such that the imaging data obtained has a particular orientation. Gradient coils 146, 148 may be positioned around a common central axis with primary magnet 142, and may be displaced from one another along the central axis. This displacement may create a gap, or window, between coils 146, 148. In an embodiment in which primary magnet 142 also includes central window 144 between coils, the two windows are aligned with one another.

Medical imaging device 140 may additionally include an RF system which may cause the protons to alter their alignment relative to the magnetic field. When the RF electromagnetic field is turned off the protons return to the original magnetization alignment. These alignment changes create a signal which can be detected by scanning. The RF system may include a single coil that both transmits the radio signals and receives the radio signals reflected from the patient. In other embodiments, the RF system may also include separate coils dedicated to the transmitting and receiving functions. In still other embodiments, the RF system may include multi-element phased array coils. Control circuitry (not depicted in FIGS. 1A and 1B) may control operation of the various coils 142, 146, 148 and the RF system, and signal-processing circuitry may receive the radio signals output by the RF system that may then be used to generate images of patient 110 supported by couch 180.

System 100 may additionally include radiotherapy device 120, which may deliver doses of radiation to patient 110 supported by couch 180. Radiotherapy device 120 may include a beam generator 124 (e.g. an x-ray source and a linear accelerator) and a beam shaping device (e.g. multi-leaf collimator (MLC)) 126, at least one of which may be mounted on a chassis 122. Chassis 122 may be powered by one or more chassis motors such that it is continuously rotatable around couch 180 when it is inserted into the treatment area. In some embodiments, a radiation detector may also be mounted on chassis 122, such as opposite beam generator 124 and with the rotational axis of chassis 122 positioned between them. Radiotherapy device 120 may additionally include control circuitry, which may be integrated within system 100 and which may control beam generator 124, MLC 126, and the chassis motor. Beam generator 124 may be positioned to emit a beam of radiation 128 through the window defined by the two gradient coils 146, 148, and also through the window 144 defined in primary magnet 142. Radiation beam 128 may be a cone beam or a fan beam, for example. In other embodiments, radiotherapy device 120 may include more than one beam generator and/or more than one respective multi-leaf collimator.

In operation, patient 110 may be placed on couch 180 and couch 180 may be inserted into the treatment area defined by magnetic coils 146, 148 and by chassis 122. Control circuitry may control beam generator 124, MLC 126, and the chassis motor to deliver radiation to the patient through the window between the coils 146, 148. The chassis motor may be controlled such that chassis 122 may rotate about the patient, such that radiation may be delivered from different directions around the patient. MLC 126 may have a plurality of elongate leaves oriented orthogonal to the axis of beam 128; an example is illustrated and described in European patent application EP-A-0,314,214, the content of which is hereby incorporated by reference and to which the reader is directed in order to obtain a full understanding of the described embodiment. The leaves of MLC 126 may be controlled to take different positions to selectively block some or all of radiation beam 128, thereby altering the shape of the beam that reaches the patient.

Simultaneously with rotation of chassis 122 about the patient, couch 180 may be moved along a translation axis into or out of the treatment area (i.e. parallel to the axis of rotation of the chassis). With this simultaneous motion, a helical radiation delivery pattern known in the art may be achieved for producing certain types of dose distributions.

The patient 110, reclining on couch 180, may be provided with an active breathing controller (ABC) 160. ABC 160 may include a breathing tube 162 which may be placed in the patient's mouth. A nasal clip 164 may be placed over the patient's nose to ensure that all breathing by the patient must be through the breathing tube 162, which may be connected to a hose 166 through which fresh air, oxygen, or a breathable mix may be supplied. Alternatively or additionally, breathing tube 162 may open to the atmosphere. Breathing tube 162 may additionally include a selectively-operable valve 168 which may close or open breathing tube 162 to selectively allow free passage of air. In some embodiments, valve 168 may be controlled via a cable extending alongside and carried by hose 166. ABC 160 may additionally include a respiration sensor 240, such as a spirometer and/or a pneumotach, which may measure the flow rate of air to and from the patient, as well as lung air volume, and which may output the measurements to system 100. Optionally, ABC 160 may further include an alarm button (not depicted in FIGS. 1A and 1B) used to cause valve 168 to immediately open and imaging and/or radiotherapy to cease.

Figure 2:
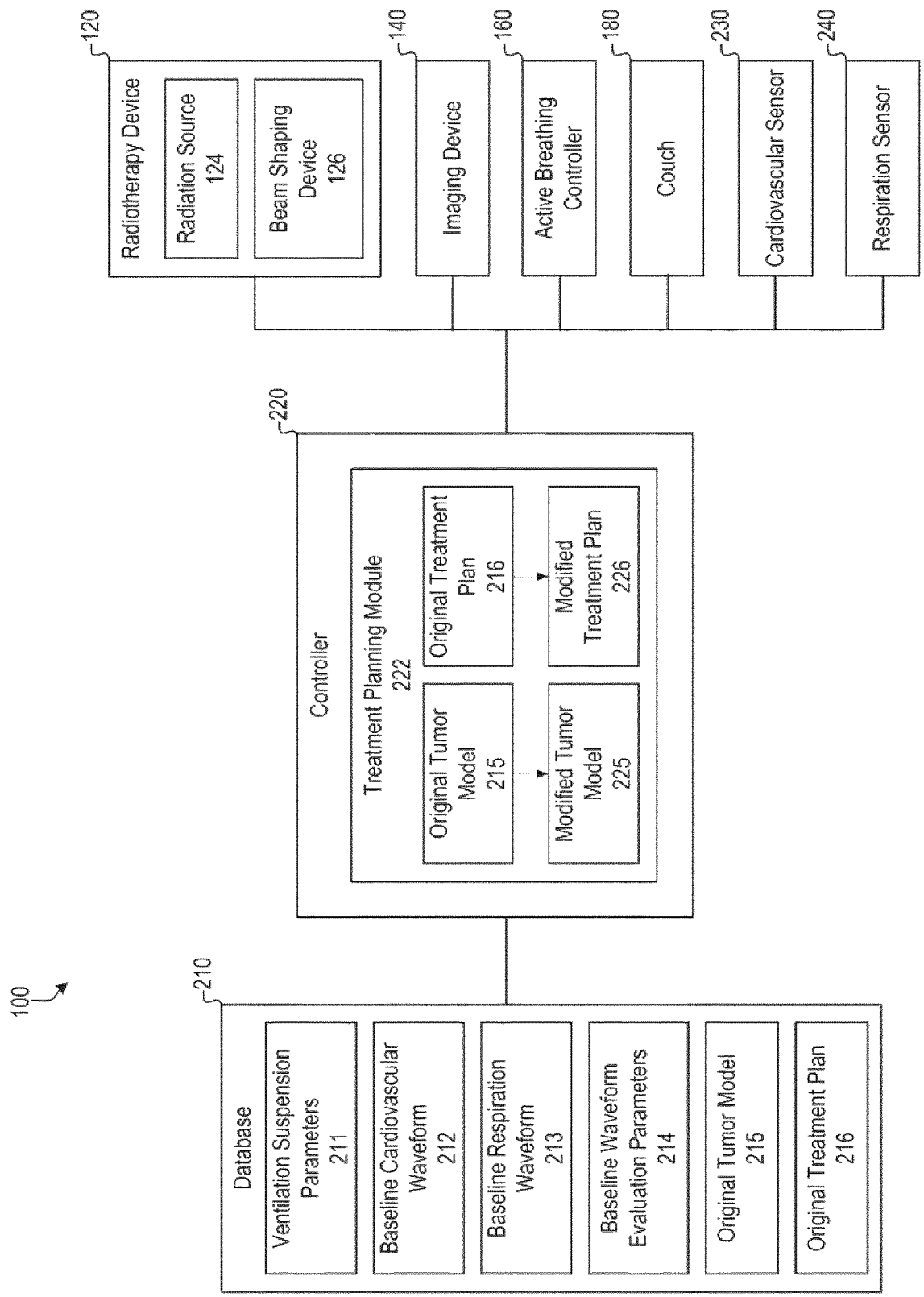

FIG. 2 illustrates another exemplary view of system 100, according to various embodiments of the present disclosure. As depicted in FIGS. 1A and 1B, system 100 may include radiotherapy device 120, imaging device 140, ABC 160, and couch 180. System 100 may additionally include a database 210 and a controller 220. Controller 220 may include hardware and software components to connect to and control various components of system 100, including and not limited to radiotherapy device 120, imaging device 140, ABC 160, and couch 180. Alternatively or additionally, controller 220 may perform functions or operations such as treatment planning, treatment execution, image acquisition, image processing, motion tracking, motion management, or other tasks involved in a radiotherapy process. The hardware components may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. The software components may include operation system software, application software, etc. For example, as shown in FIG. 2, controller 220 may include treatment planning module 222 that may be stored in a memory/storage device of controller 220. Module 222 may include computer readable and executable codes or instructions. A processor of controller 220 may be communicatively connected to treatment planning module 222 to access and execute the codes or instructions. The execution of the codes or instructions may cause controller 220 to perform operations to achieve one or more functions consistent with the disclosed embodiments.

Imaging device 140 may provide medical images of a patient. For example, imaging device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, imaging device 140 may include an MRI imaging device, a CT imaging device, a PET imaging device, an ultrasound imaging device, a fluoroscopic device, a SPECT imaging device, or other medical imaging devices for obtaining the medical images of the patient. Imaging device 140 can be configured to acquire one or more images of the patient's anatomy for a region of interest (e.g., a target organ, a target tumor or both). Each image, typically a 2D or 3D image slice, can include one or more parameters (e.g., a slice thickness or volume, an orientation, and a location, etc.). In an example, the imaging device 140 may acquire an image slice in any orientation. For example, an orientation of the image slice can include a sagittal orientation, a coronal orientation, or an axial orientation. Controller 220 may adjust one or more parameters, such as the size and/or orientation of the image slice, to include the target organ and/or target tumor. In an example, image slices can be determined from information such as a 3D MRI volume. Such image slices can be acquired by the imaging device 140 in "real-time" while a patient is undergoing radiation therapy treatment, for example, when using radiotherapy device 120.

Radiotherapy device 120 may include a LINAC or any other suitable device capable of delivering radiation to an anatomical region of interest of a patient in a controllable manner. Controller 220 may control radiotherapy device 120 according to a radiotherapy treatment plan. The treatment plan may include information about a particular dose to be applied to a particular patient, as well as other parameters such as beam angles, dose-histogram-volume information, the number of radiation beams to be used during therapy, the dose per beam, and the like. Controller 220 may control various components of radiotherapy device 120, such as chassis 122, beam generator 124, and beam shaping device 126, according to the treatment plan. In some embodiments, controller 220 may generate a treatment plan using images received from imaging device 140. Alternatively or additionally, controller 220 may acquire a treatment plan from database 210 and may execute the plan with radiotherapy device 120. In some embodiments, controller 220 may modify a treatment plan received from database 210 prior to execution with radiotherapy device 120.

Controller 220 may additionally control operation of ABC 160 during one or more of an imaging session and a radiotherapy session. Controller 220 may control various ventilation suspension parameters of ABC 160, such as a duration and number of valve closure periods ("breath-hold periods") and a point in the patient's respiration cycle in which the valve of ABC 160 is closed. In some embodiments, controller 220 may receive ventilation suspension parameters for a given patient from database 210 and may use the parameters to control ABC 160. In the event that the patient actuates the alarm button of ABC 160, controller 220 may cause opening of valve 168, as well as to halt operation of radiotherapy device 120 and/or imaging device 140.

In some embodiments, controller 220 may receive data from respiration sensor 240 relating to the patient's respiration cycle, and may use the data to control ABC 160. In some embodiments, sensor 240 may include a pneumotach, which may collect data relating to the rate of airflow during respiration. Sensor 240 may output the sensed respiration data to controller 220 for processing. In some embodiments, controller 220 may process the data to identify the patient's respiration cycle, including the end of exhalation ("end-exhalation") and/or the end of inhalation ("end-inhalation"). Alternatively or additionally, controller 220 may process the respiration data to evaluate the volume of air in the patient's lungs during the respiration cycle. Controller 220 may use the processed respiration data to output control signals to ABC 160 to perform breath-holding. For example, controller 220 may transmit a ventilation suspension signal to ABC 160 to close valve 168 at a specified point in the patient's respiration cycle, for example at end-exhalation. Controller 220 may process data from respiration sensor 240 to identify when end-exhalation occurs. For example, end-exhalation may be identified when the patient's lungs are determined to hold a specified volume of air. Alternatively or additionally, end-exhalation may be identified by a change in airflow direction (i.e. the end of exhalation and the beginning of inhalation). One of ordinary skill in the art will appreciate that end-inhalation may be identified using similar methods, as well as any other desired point in the patient's respiration cycle. When end-exhalation is identified, controller 220 may transmit a ventilation suspension signal to ABC 160 to close valve 168, the signal indicating the length of the breath-hold period. Alternatively or additionally, controller 220 may process data received from imaging device 140 to control ABC 160. For example, a navigator channel (or another fast-acquisition output) of imaging device 140 may execute a quick 1D or 2D scan to measure movement of the patient's diaphragm and/or movement of the target tumor, and may output the scan data to controller 220, which may process the scan data to identify end-exhalation.

Controller 220 may additionally control movement of couch 180. For example, controller 220 may control one or more of translation, rotation, and cantilever motion of couch 180 to correctly position the patient for imaging and/or radiotherapy. In some embodiments, controller 220 may move couch 180 to a specified position as part of a treatment plan. Alternatively or additionally, controller 220 may move couch 180 to compensate for the patient assuming a different position upon couch 180 during different stages of planning and treatment. That is, should a patient lie differently on couch 180 during treatment than they did during planning, controller 220 may move couch 180 so that the patient is moved into the desired position. Controller 220 may achieve this repositioning, for example, by utilizing imaging data received from imaging device 140.

System 100 may additionally include at least one cardiovascular sensor 230. Cardiovascular sensor 230 may include, for example, one or more of an electrocardiography (ECG) sensor and a pulse oximeter. In some embodiments, signals measured by cardiovascular sensor 230 may be used to evaluate and monitor the patient's breathing during imaging and/or radiotherapy because cardiovascular activity is dependent upon the patient's respiration. Thus, signals measured by cardiovascular sensor 230 and respiration sensor 240 may indicate changes in the patient's respiration and respiratory movement. Advantageously, the use of multiple parameters may provide more comprehensive and sensitive monitoring of the patient, since the likelihood of undetected respiratory episodes is greatly reduced by the measurement redundancy. According to various embodiments in which sensor 230 includes an ECG sensor, the ECG electrodes may be positioned upon the patient's body according to known configurations. In some embodiments, sensor 230 may be configured so as to minimize or eliminate interference with MRI. For example, electrodes of sensor 230 may be configured to operate with a frequency which is different from the transceiver frequency of an MR imaging device (e.g. imaging device 140) such that MRI artifacts can be minimized. Alternatively or additionally, an electronic filter may be added at the sensor output of sensor 230 to reduce noise emitted therefrom. Alternatively or additionally, as explained below with reference to FIG. 9, communication lines between various components of system 100 may be established using, for example, optical fibers or wireless techniques, so as to reduce noise produced by traditional electronic cabling. According to various embodiments in which sensor 230 includes a pulse oximeter, the pulse oximeter may be attached to various portions of the patient's body, such as a finger or toe. Advantageously, such placement may position the pulse oximeter outside the treatment area of system 100. As a result, the pulse oximeter may avoid being damaged or otherwise interfered with by radiotherapy device 120 or by imaging device 140.

Controller 220 may be communicatively connected to database 210 to access data. In some embodiments, database 210 may be implemented using local hardware devices, such as one or more hard drives, optical disks, and/or servers that are in the proximity of controller 220. In some embodiments, database 210 may be implemented in a data center or a server located remotely with respect to controller 220. Controller 220 may access data stored in database 210 through wired or wireless communication.

Database 210 may include data pertaining to operation of ABC 160, which may have been collected during a session prior to a radiotherapy session with radiotherapy device 120. For example, database 210 may include ventilation suspension parameters 211 for one or more patients. As explained below, parameters 211 may be utilized to control operation of ABC 160. Database 210 may additionally include various baseline physiological measurement signals, such as a baseline cardiovascular signal 212, a baseline respiration signal 213, and baseline signal evaluation parameters 214. A signal may include, for example, a value, a waveform, etc. As explained below, signals 212-214 may be collected from the patient during a prior session and may serve as baselines against which data collected during radiotherapy may be compared. Database 210 may additionally include a tumor model 215 and a radiotherapy treatment plan 216, which may have been generated from imaging data collected by an imaging device and/or a combination imaging and radiotherapy system. In some embodiments, controller 220 may generate tumor model 215 and treatment plan 216 (using, for example, imaging data collected by imaging device 140), and may send tumor model 215 and treatment plan 216 to database 210 for storage therein. In other embodiments, tumor model 215 and treatment plan 216 may be generated by a processor outside of system 100 and may be stored in database 210. In such a case, controller 220 may receive tumor model 215 and treatment plan 216 from database 210 and may execute a radiotherapy session with radiotherapy device 120 according to the received tumor model 215 and treatment plan 216.

In some embodiments, controller 220 may include treatment planning module 222. Module 222 may receive tumor model 215 and treatment plan 216, such as from database 210, and may modify tumor model 215 to produce modified tumor model 225. In some embodiments, prior to the start of a radiotherapy session, system 100 may collect a number of images with imaging device 140. The images may be compared against tumor model 215 to determine changes to the target tumor, such as changes in target tumor size or location. Module 222 may modify tumor model 215 to incorporate the determined changes to the target tumor, thus producing modified tumor model 225. Treatment plan 216 may also be modified to account for the determined changes in the tumor, thus producing modified treatment plan 226. The radiotherapy session may be executed according to modified treatment plan 226. However, one of ordinary skill in the art will appreciate that controller 220 may additionally or alternatively execute treatment plan 216 as received from database 210, without modification by module 222.

Figure 3:
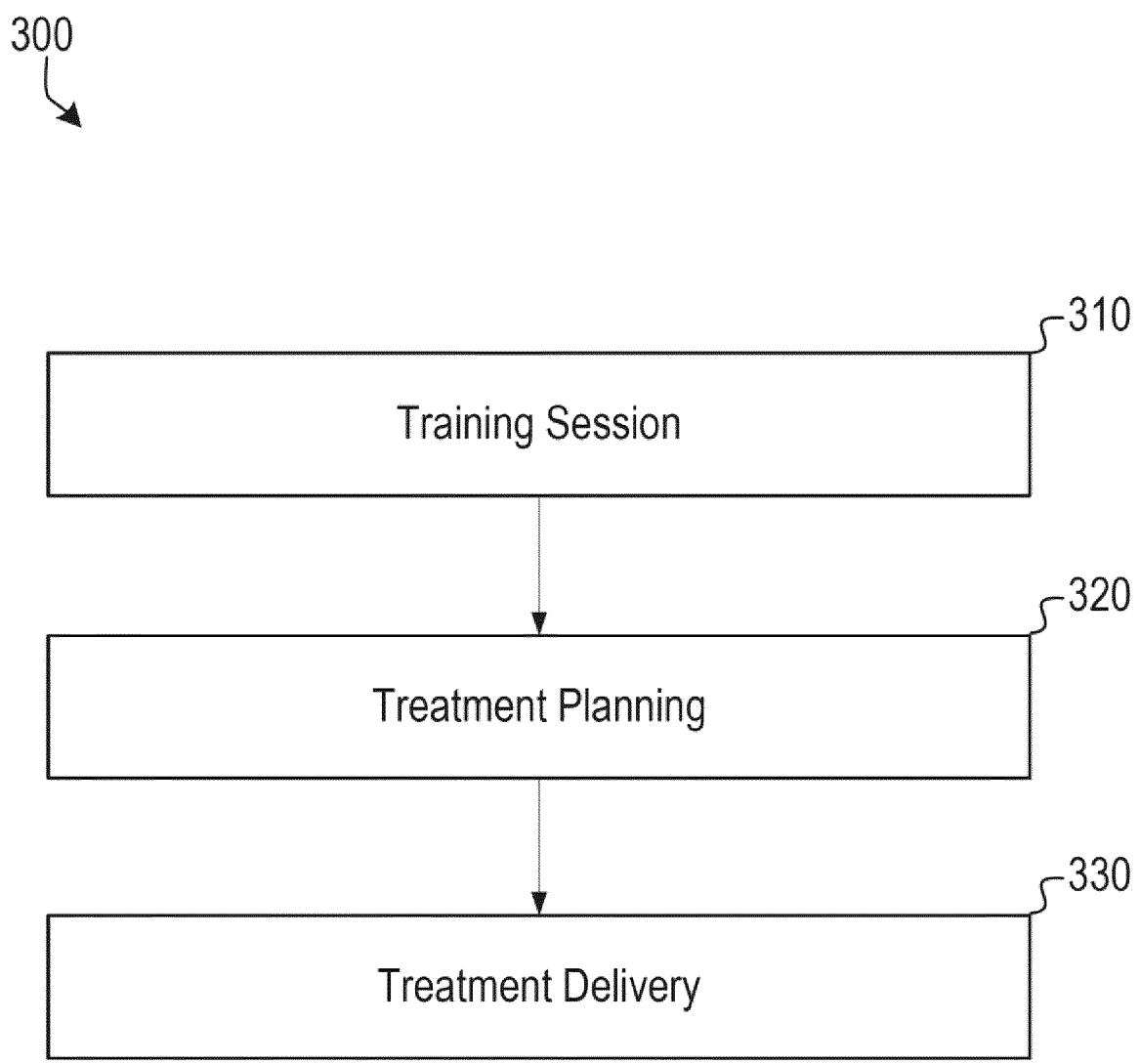
FIG. 3 illustrates a flow diagram of an exemplary method for developing a reproducible breath-hold pattern for performance during image-guided radiotherapy, according to various embodiments of the present disclosure.

FIG. 3 illustrates an exemplary method 300 for developing a reproducible breath-hold pattern for performance during image-guided radiotherapy. Method 300 may include a training session 310, a treatment planning session 320, and a treatment delivery session 330. Method 300 may be a processor-executed method. In some embodiments, sessions 310-330 may be executed by the same processor, such as controller 220. Alternatively, one or more of sessions 310-330 may be executed by separate processors. According to various embodiments one or more processors, such as controller 220, may execute method 300 to permit a patient to develop and practice a reproducible breath-hold pattern prior to treatment planning and radiotherapy. As a result, the patient may be more comfortable during radiotherapy, and better able to perform the established breath-hold pattern within accepted quality limits. Additionally, one or more processors may execute method 300 to measure baseline cardiovascular and respiratory signals which may be indicative of reproducible breath-holding. For example, baseline signals may be collected by various sensors from the patient during a training session 310 in which the patient's preferred breath-hold pattern is established. During a subsequent treatment planning session 320 and/or treatment delivery session 330, cardiovascular and respiratory signals may be measured from the patient and compared to the baseline signals. Differences between the measured signals and baseline may indicate unreproducible breath-holding.

Figure 4:
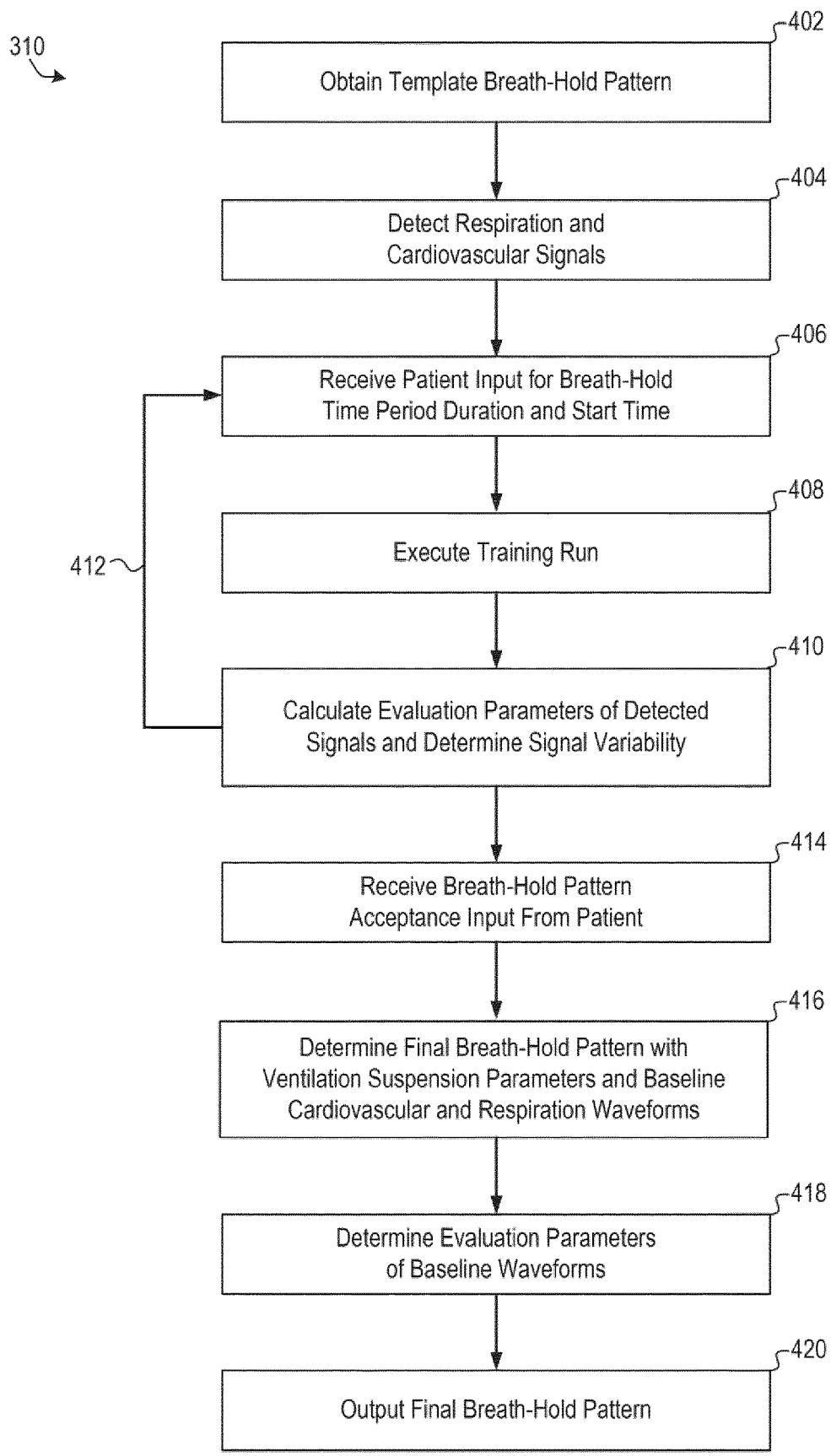
FIG. 4 illustrates a flow diagram of an exemplary training session, according to various embodiments of the present disclosure.
Figure 5:
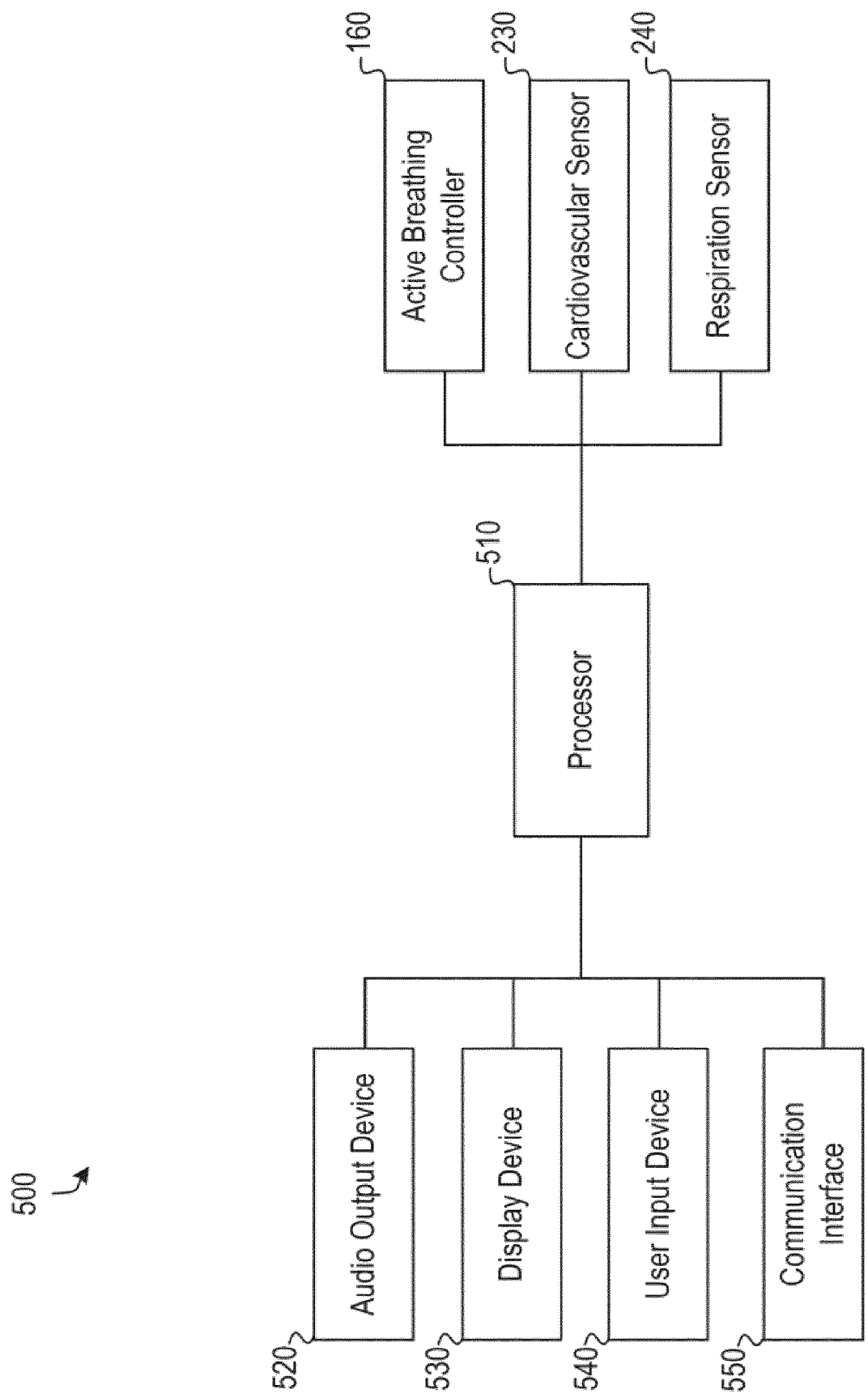
FIG. 5 illustrates an exemplary training session system, according to various embodiments of the present disclosure.

FIG. 4 illustrates exemplary steps performed during a training session 310, and FIG. 5 illustrates an exemplary training session system 500, which may include processor 510. Training session 310 may be executed by a processor and may be performed with ABC 160 and sensors 230, 240. The following example describes execution of training session 310 by processor 510. However, training session 310 may additionally or alternatively be executed by controller 220 or by any suitable processor.

In some embodiments, processor 510 may perform training session 310 in a non-clinical environment, such as in the patient's home without a physician or practitioner present. Advantageously, this may reduce the overall cost of the patient's treatment because training session 310 need not be performed in a clinical setting or with a medical practitioner. In some embodiments, processor 510 may be a desktop or laptop computer in the patient's home and may output data collected during training session 310 to a storage device via communication interface 550. Processor 510 may be configured to send control signals to and to receive feedback signals from ABC 160 and sensors 230, 240.

During training session 310, processor 510 may allow the patient to practice a breath-hold pattern with ABC 160 until the patient becomes comfortable performing it and the breath-hold pattern becomes reproducible. That is, processor 510 may repeat execution of the breath-hold pattern with ABC 160 until the patient is able to hold their breath for a consistent length of time and at a consistent point in their respiratory cycle for each breath-hold. Training session 310 may be performed by processor 510 to determine a breath-hold pattern for execution by ABC 160 which the patient may comfortably and reproducibly perform during imaging and/or radiotherapy. The patient may practice the breath-hold pattern a number of times during training session 310 until they are able to perform it in a reproducible fashion, with consistent breathing frequency, lung volumes (and thus chest position), and duration of the breath-hold. By achieving a reproducible breath-hold pattern, processor 510 may ensure that the patient's anatomy, and well as a target tumor, are positioned in the same location during each breath-hold. Advantageously, when a processor executes the reproducible breath-hold pattern with the patient during a subsequent radiotherapy session, radiation delivered by radiotherapy device 120 may be accurately delivered to the target tumor and not to healthy surrounding tissue. During the course of training session 310, processor 510 may adjust or allow the patient to adjust the parameters of the breath-hold pattern until the patient can reliably reproduce a desired pattern.

In some embodiments, system 500 may include one or more audio output devices 520, such as speakers or headphones, as well as a display device 530 to provide feedback to the patient during training session 310. In some embodiments, processor 510 may provide visual instructions to the patient via display device 530 to guide the patient during performance of training session 310. Alternatively or additionally, processor 510 may provide a telephone or video chat option through audio output device 520 and/or display device 530 so that the patient may interact with a practitioner, such as a physician or nurse. Training session 310 may be executed by processor 510, with ABC 160 and sensors 230, 240 arranged on the patient in the proper clinical configuration. In some embodiments, audio output device 520 may output audio guidance to the patient for training session 310. For example, device 520 may alert the patient of an upcoming breath-hold. Optionally, device 520 may additionally output relaxing audio (e.g. ocean sounds). As sensors 230, 240 collect measurements from the patient during the training session 310, feedback signals therefrom may be displayed on display device 530. System 500 may also include user input device 540 and communication interface 550, which may be communicatively coupled to processor 510. Input device 540 may include, for example, keyboards, mice, touch screens, mics, buttons, knobs, trackballs, levers, handles, and joysticks. Communication interface 550 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a Wi-Fi adaptor), a telecommunication adaptor (e.g., 3G, 4G/LTE and the like), and the like.

According to Step 402 of the training session, processor 510 may obtain a template breath-hold pattern, such as via interface 550, and may store it in a memory storage device as the patient's breath-hold pattern. The template may include a preset duration of the breath-hold periods, as well as a preset point in the patient's respiration cycle in which the breath-holds are to occur. For example, the breath-holds may occur at end-inhalation or at end-exhalation. In some embodiments, the template breath-hold pattern may be a standard template. Alternatively, the template breath-hold pattern may be determined according to one or more characteristics of the patient. For example, processor 510 may access a database of breath-hold pattern templates via interface 550 and may select a template according to the patient's sex, age, weight, height, chest size, medical conditions, etc. During training session 310, the template breath-hold pattern may be modified and personalized for the patient according to the patient's feedback and signals detected by sensors 230, 240.

In Step 404, sensors 230, 240 may collect physiological data from the patient. Sensor 230 may collect a cardiovascular signal, such as one or more of an ECG signal and a $SpO_2$ signal. Sensor 240 may collect a respiration signal, such as a signal indicating airflow to and from the patient through hose 166 of the ABC. Sensors 230, 240 may output their respective measured signals to processor 510 for processing and analysis.

In Step 406, processor 510 may receive input data from the patient about their desired breath-hold period parameters, such as through input device 540. For example, processor 510 may receive data reflecting a selection by the patient to lengthen or shorten the duration of the breath-hold period. Processor 510 may also receive data from the patient which may reflect a selection for the breath-hold to occur at end-expiration, end-inhalation, or both. Processor 510 may modify the patient's breath-hold pattern according to the received input. In some embodiments, in the event that processor 510 does not receive input data in Step 406, processor 510 may maintain the breath-hold parameters from the template breath-hold pattern received in Step 402 and/or from a previous training run.

In Step 408, processor 510 may execute a training run in which the patient may practice the breath-hold. The patient may assume a supine position, similar to how they might be positioned during imaging or radiotherapy. Breathing tube 162 may be placed in the patient's mouth, with nasal clip 164 clamped over the nose. In some embodiments, the patient may hold the panic button in a hand. Processor 510 may output audio guidance through audio output device 520 to notify the patient of the beginning of the training run, the start of one or more breath-holds, and/or of a remaining duration of the training run. As sensors 230, 240 output data to processor 510, feedback signals may be displayed on display device 530 for viewing by the patient. During the training run, processor 510 may monitor signals received from respiratory sensor 240 to identify the determined point in the patient's respiratory cycle in which the breath-hold occurs. Upon detecting this point, processor 510 may send a ventilation suspension signal to ABC 160, which may close valve 168 for the determined breath-hold period duration, after which time valve 168 may be opened. In some embodiments, processor 510 may execute a single breath-hold cycle during a training run. In some alternative embodiments, processor 510 may execute a predetermined number of breath-hold cycles (e.g. 3, 5, 10, 15, 20, 25, 30, etc.) during a training run. In some still further embodiments, processor 510 may continuously execute breath-hold cycles until stopped by the patient, such as through operation of user input device 540 or the panic button. Throughout training run 408, sensors 230 and 240 may continuously output data to processor 510. At any time, should the patient actuate the panic button, the training run may be halted and valve 168 may be opened.

Figure 6A:
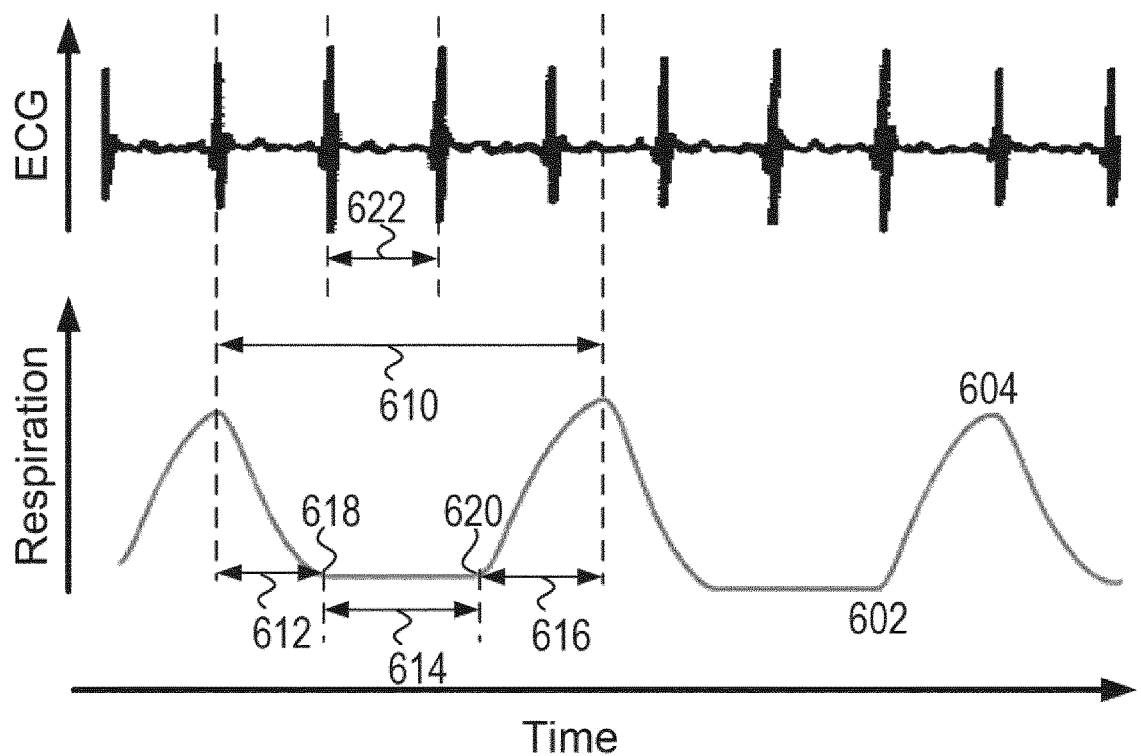
FIG. 6A illustrates exemplary respiratory and electrocardiogram (ECG) signals during breath-holding, according to various embodiments of the present disclosure.
Figure 6B:
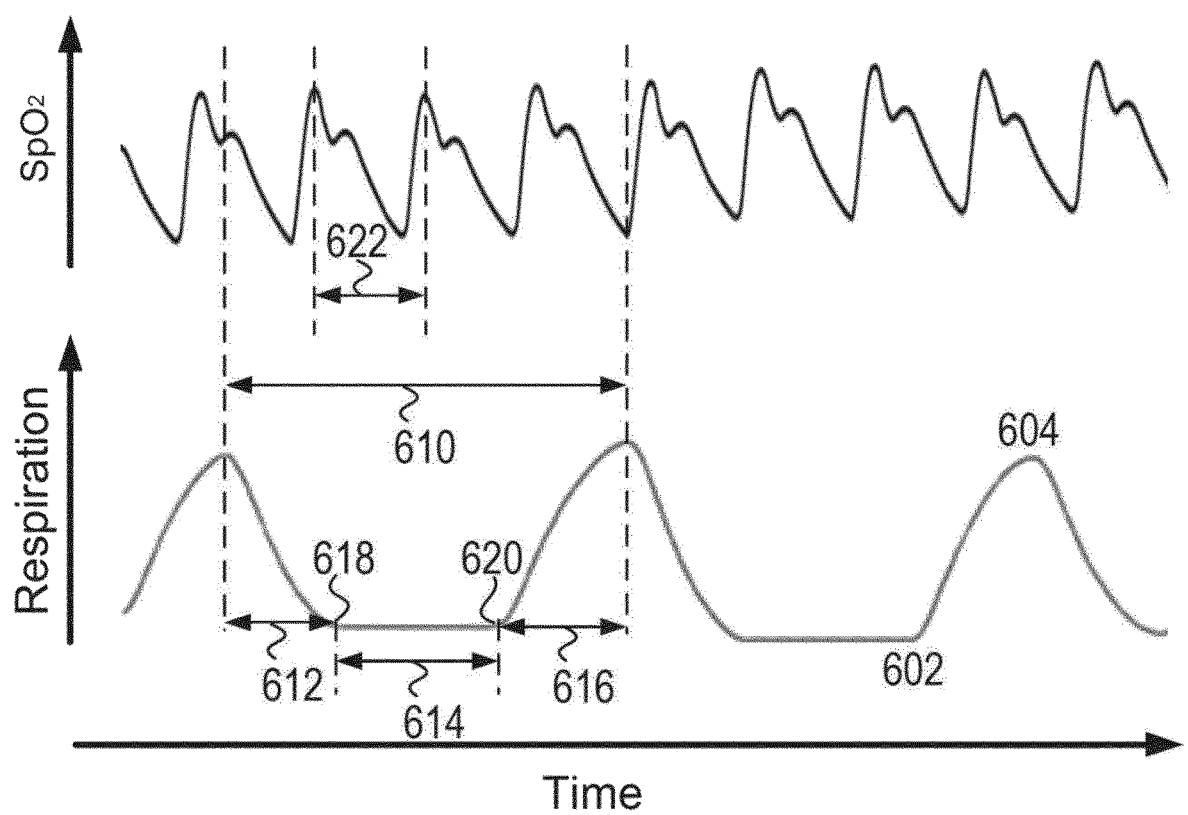
FIG. 6B illustrates exemplary respiratory and peripheral capillary oxygen saturation ($SpO_2$) signals during breath-holding, according to various embodiments of the present disclosure.

In Step 410, processor 510 may process signals received from sensors 230, 240 during training run 408 to generate evaluation parameters thereof. FIG. 6A illustrates various evaluation parameters for exemplary ECG and respiratory signals, while FIG. 6B illustrates various evaluation parameters for exemplary $SpO_2$ and respiratory signals. However, according to some embodiments, both ECG and $SpO_2$, as well as any other suitable cardiovascular signal, may be measured by sensor 230. The exemplary respiratory signal may oscillate cyclically between end-exhalation 602 and end-inhalation 604. In some embodiments, end-exhalation 602 and end-inhalation 604 may each be associated with pre-determined lung volumes, at one or more of which the breath-hold may be programmed to occur. FIGS. 6A and 6B illustrate an embodiment in which the breath-hold occurs at end-exhalation 602. However, processor 510 may be configured to control ABC 160 such that the breath-hold instead occurs at end-inhalation 604.

Processor 510 may calculate respiration cycle duration 610, which may be the period of the cyclical respiration cycle. For example, respiration cycle duration 610 may be calculated as the length of time between two consecutive end-exhalations 602 or between two consecutive end-inhalations 604. Additionally, processor 510 may calculate the breath-hold period duration 614, which may be associated with the length of time in which valve 168 of the ABC is closed, and the length of time in which the patient's chest is held in the breath-hold position. Duration 614 may be determined as a duration in which the respiration cycle is held constant due to lack of airflow to or from the patient through ABC 160. Start time 618 may be determined as the start of the breath-hold, coinciding with the time at which processor 510 may send a ventilation suspension signal to ABC 160. End time 620 may be determined as the end of the breath-hold, at which point valve 168 may be opened and respiration may resume. Thus, duration 614 may be the amount of time between start time 618 and end time 620.

According to the embodiment illustrated in FIG. 6A, processor 510 may further determine exhalation falling time 612, which may be the time period between end-inhalation 604 and the subsequent breath-hold start time 618, as well as inhalation rising time 616, which may be the time period between breath-hold end time 620 and the subsequent end-inhalation 604. According to alternative embodiments in which the breath-hold occurs at end-inhalation 604, processor 510 may determine inhalation rising time 616 as the time period between end-exhalation 602 and the subsequent breath-hold start time 618. Similarly, processor 510 may determine exhalation falling time 612 as the time period between breath-hold end time 620 and the subsequent end-exhalation 602. In some embodiments, respiration cycle duration 610 may equal the combined durations of exhalation falling time 612, breath-hold period duration 614, and inhalation rising time 616.

Processor 510 may additionally analyze the cardiovascular signal detected from sensor 230 to determine evaluation parameters thereof. According to embodiments in which the cardiovascular signal includes an ECG signal, such as the example of FIG. 6A, processor 510 may determine the duration 622 of a single ECG cycle. For example, processor 510 may determine the length of time between two consecutive ECG phenomena, such as the length of time between two consecutive R-waves or two consecutive S-waves. Thus, processor 510 may calculate the patient's heart rate, such as in beats per minute (BPM). Processor 510 may additionally determine the duration and amplitude of the signals of the ECG cycle, as well as the duration of intervals between them. According to embodiments in which the cardiovascular signal includes an $SpO_2$ signal, such as the example of FIG. 6B, processor 510 may determine the duration 622 of a single $SpO_2$ cycle, which may be utilized to determine the pulse rate and heart rate. In some embodiments, processor 510 may additionally calculate a ratio between cardiovascular cycle duration 622 and one or more of respiration cycle duration 610, exhalation falling time 612, breath-hold period duration 614, and inhalation rising time 616.

Returning to Step 410 of FIG. 4, processor 510 may calculate one or more evaluation parameters and may determine their variability during the training run. For example, processor 510 may calculate one or more of the range, mean, variance, standard deviation, and percent difference for one or more evaluation parameters. In some embodiments, processor 510 may utilize machine learning techniques to develop a model of the patient's breath-holding. In the event that the calculated variability of one or more parameters is above a pre-determined threshold (e.g. a difference of 5%), the breath-hold pattern performed during the last training run may be determined to be unreproducible. A number of factors may contribute to unreproducible breath-holding, such as a patient's discomfort or unfamiliarity with operation of the ABC, or exploration by the patient of their preferred breathing pattern. In other cases, the patient may become anxious during a training run, which may cause their cardiovascular and respiration cycles to increase in frequency. In some yet further cases, the patient may become fatigued during the course of a training run and may breathe more frequently and with more shallow breaths. Whatever the case, training run data with too high a variability of one or more evaluation parameters may be rejected by processor 510 because it may indicate unreproducible breath-holding. At the end of Step 410, processor 510 may elect to store the detected cardiovascular and respiratory signals in the memory storage device. Alternatively or additionally, processor 510 may elect to store the evaluation parameters therefrom.

When processor 510 determines that the patient did not achieve reproducible breath-holding, processor 510 may elect to perform another training run, as indicated by Step 412. Prior to the subsequent training run, the patient may choose to alter one or more parameters of the breath-hold pattern at Step 406. For example, the patient may elect to change the length of the breath-hold. Alternatively, the patient may choose to leave the ventilation suspension parameters unchanged. Processor 510 may then execute another training run at Step 408, and the signals measured therefrom may be evaluated at Step 410. Optionally, at Step 410 processor 510 may compare the evaluation parameters from a current training run to parameters from prior training runs, to evaluate their inter-trial variation. In some embodiments, this process may continue until processor 510 determines at Step 410 that the patient has achieved a reproducible breath-hold pattern. In some embodiments, this determination may be made when the measured variability of all evaluation parameters are below the pre-determined threshold, thus suggesting that the breath-hold pattern was reproducible during the training run. Optionally, processor 510 may also consider the variation of the evaluation parameters between training runs. For example, processor 510 may not determine a breath-hold pattern to be sufficiently reproducible until variation between trials is below a threshold. In some embodiments, data collected during multiple or all training runs may be incorporated into a machine learning model which may be executed by processor 510 to establish the patient's breath-hold pattern. For example, such a machine learning model may be based upon a maximum likelihood estimation, which may reflect the confidence level of the similarity between training run data and previous data. Optionally, processor 510 may query the patient at Step 414 if they would like to keep the reproducible breath-hold pattern, or if they would like to return to Step 406 to perform another training run.

At Step 416, the final, reproducible breath-hold pattern for the patient may be established and stored in the memory storage device, the pattern including the corresponding ventilation suspension parameters 211. Processor 510 may additionally receive the cardiovascular signal which was detected by sensor 230 during the reproducible breath-holding, and may store this signal in the memory storage device as baseline cardiovascular signal 212. Processor 510 may similarly receive the respiration signal detected by sensor 240 during the reproducible breath-holding, and may store it in the memory storage device as baseline respiration signal 213. Because these signals were measured during reproducible breath-holding, they may serve as baselines against which subsequent signals may be compared to determine if the reproducible breath-hold pattern is achieved. At Step 418, processor 510 may calculate and store the evaluation parameters 214 of the baseline signals in the memory storage device.

At Step 420, processor 510 may output the final breath-hold pattern and the associated baseline signals and evaluation parameters, such as via interface 550. This data may be outputted to a suitable data storage site from which it may be accessed for subsequent evaluation and use. For example, the data may be outputted to a database, such as database 210, from where it may be accessed by another processor such as controller 220. The data may also be uploaded to a cloud server, network device, or processor, and may also be sent to a physician, or to a hospital or health system database. In some embodiments, the final breath-hold pattern, as well as qualifying characteristics of the patient, may be added to the database of breath-hold pattern templates, e.g. via interface 550.

Advantageously, because processor 510 may permit the patient to select their desired breath-hold pattern and provide the patient with the opportunity to practice the pattern during training session 310, processor 510 may allow the patient to be more comfortable performing the pattern in subsequent imaging or radiotherapy sessions, and less likely to stray from the established pattern. Additionally, execution of the reproducible breath-hold pattern by a processor such as controller 220 in future sessions may allow more precise imaging and more accurate radiation delivery, since the target tumor is consistently held in the same location by the processor for each breath-hold and because the patient can comfortably hold the entire breath-hold duration.

Cardiovascular and respiratory signals detected by sensors 230, 240 are dependent upon and reflect changes in the patient's respiration cycle. The monitoring of multiple respiration-dependent parameters by processor 510 may allow more accurate detection of changes in the patient's respiration and respiratory movement. In some cases, changes in respiratory movement may be difficult to detect from the respiratory signal alone. Thus, the cardiovascular signal may provide processor 510 with an additional metric for evaluation of the patient's respiration. For example, in the event that a patient panics during a breath-hold, their breathing may become faster and shallower and their heart rate may race. Output from respiration sensor 230 may not immediately indicate these changes, since a respiration cycle has a longer duration of approximately 3.5 seconds. Thus, in some cases several seconds may need to be provided for variation in the respiration cycle to be registered by processor 510. However, the cardiovascular signal has a shorter cycle duration of approximately one second. Thus, variation in the cardiovascular signal may be detected by processor 510 after only a few seconds, after which time processor 510 may conclude that breath-holding is no longer reproducible.

In some embodiments, processor 510 may calculate ratios between the cardiovascular and respiratory signals and may monitor them over time. For example, processor 510 may calculate evaluation parameters including the ratio between cardiovascular cycle duration 622 and respiration cycle duration 610. For example, in some patients these durations may have a 1:3.5 ratio, due to a cardiovascular cycle duration 622 of approximately one second and a respiration cycle duration 610 of approximately 3.5 seconds. In the event that processor 510 detects a change in this ratio, such as a change due to an increase in heart rate, processor 510 may determine that the patient is not performing the breath-hold pattern or that the patient is in distress. Because the evaluation parameters may include parameters detected only from each of the cardiovascular and respiratory signals, as well as parameters derived from both signals, output from cardiovascular sensor 230 may provide processor 510 with a cross-check on output from respiration sensor 240, and vice versa.

In some embodiments, processor 510 may perform training session 310 in a non-clinical environment, such as at the patient's home or workplace. Advantageously, this may reduce the overall cost of the patient's treatment because the processor need not perform training session 310 in a clinical setting or with a medical practitioner. Additionally, in some cases processor 510 may allow the patient to prolong their reproducible breath-hold period due to the practice they may receive during training session 310. This may reduce the time needed during subsequent imaging or radiotherapy sessions because images may be collected or radiation may be delivered during longer breath-holds. Further, the patient may be more relaxed and comfortable performing a breath-hold pattern of their choosing, rather than being forced to sustain an uncomfortable breath-hold pattern.

Figure 7A:
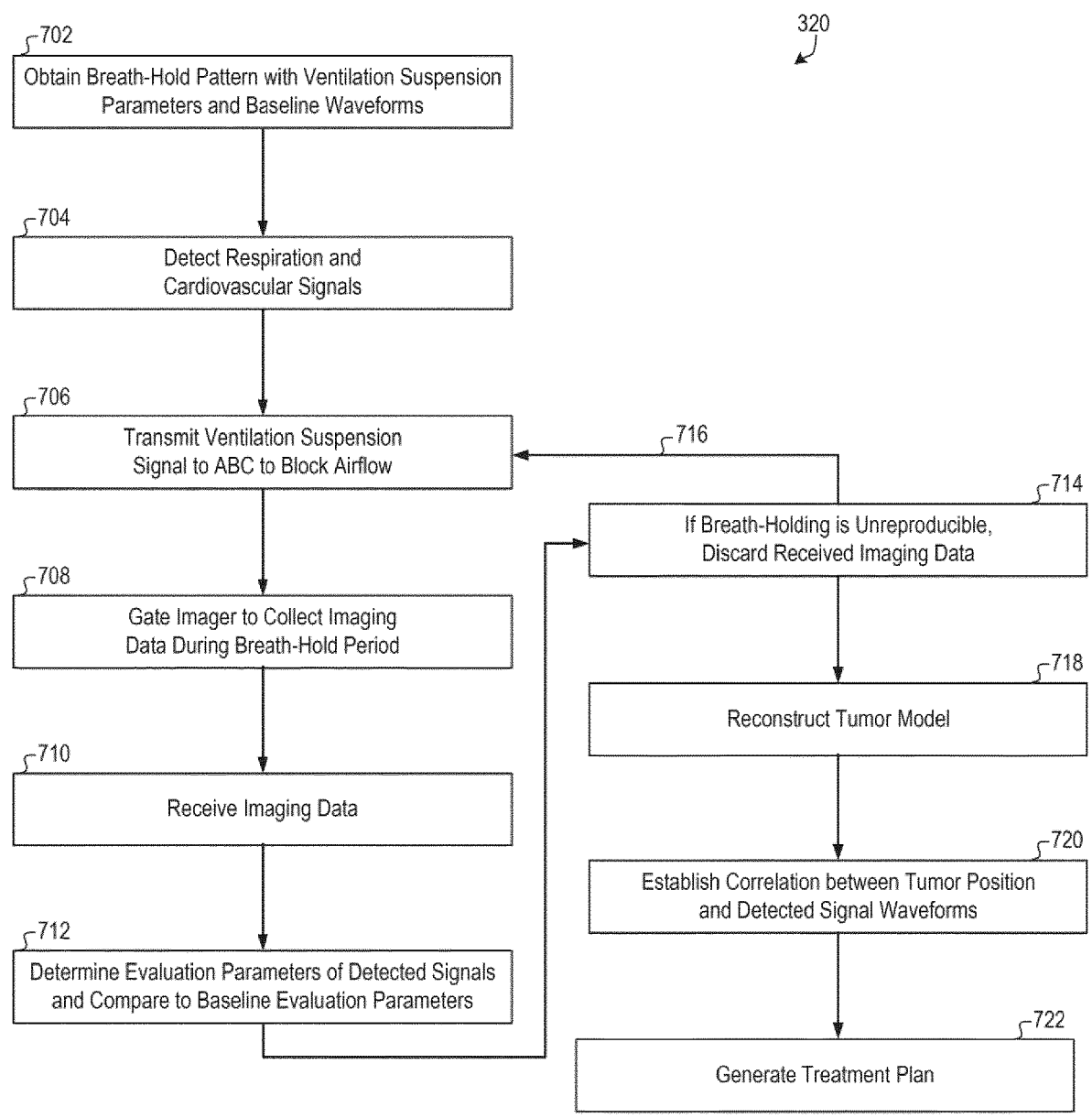
FIG. 7A illustrates a flow diagram of an exemplary treatment planning session, according to various embodiments of the present disclosure.

FIG. 7A illustrates exemplary steps performed during a treatment planning session 320, according to various embodiments. The following example describes execution of treatment planning session 320 by controller 220. However, treatment planning session 320 may additionally or alternatively be executed by any suitable processor. For example, in some embodiments treatment planning session 320 may be executed by a processor associated with an imaging device which is outside of system 100, such as an MRI system without a radiotherapy component. Performance of planning session 320 with an external device may prolong the life of system 100, since high resolution imaging for treatment planning may contribute to, for example, wearing of the MRI gradient amplifier and degrading of the RF coil. Further, performance of training session 310 and treatment planning session 320 at locations outside of system 100 may allow use of system 100 to perform image-guided radiotherapy on a larger number of patients, since time with system 100 need not be utilized for training or treatment planning. According to various embodiments in which treatment planning session 320 is performed by a processor associated with an imaging device external to system 100, one or more of ABC 160, couch 180, sensor 230, and sensor 240 may be utilized.

During session 320, images may be collected from a patient by imaging device 140 and outputted to controller 220, which may generate a model of the target tumor, from which controller 220 may create a radiotherapy treatment plan. Feedback may be provided to controller 220 by sensors 230, 240 to evaluate the patient's respiration cycle so ensure that the patient is performing the reproducible breath-hold pattern with the required accuracy. Advantageously, execution of the reproducible breath-hold pattern by controller 220 during planning session 320 may provide better quality and higher resolution images of the tumor, since controller 220 may hold the tumor in the same position in each breath-hold through gating of ABC 160, and since the breath-hold period duration may be long enough to allow high resolution 2D and 3D imaging by imaging device 140.

In Step 702, controller 220 may receive the established breath-hold pattern for the patient, which may include ventilation suspension parameters 211, as well as the baseline signals 212, 213 and evaluation parameters 214 for the patient. For example, controller 220 may receive this data from database 210 or another data storage device. In Step 704, sensors 230, 240 may collect physiological data from the patient and may output their respective measured signals to controller 220 for processing and analysis. Per the patient's established breath-hold pattern, controller 220 may monitor data received from one or more of sensors 230 and 240 to determine when the beginning of the breath-hold (e.g. end-exhalation) occurs. In Step 706, upon detection of the requisite portion of the patient's respiratory cycle, controller 220 may transmit a ventilation suspension signal to ABC 160 to close valve 168 for the duration of the breath-hold period. In Step 708, controller 220 may gate the imager of imaging device 140 (e.g. coils 142, 146, 148 and/or the MRI RF system) to collect imaging data of the patient during the breath-hold period. The imaging data may include, for example, 2D or 3D image slices of the target tumor. Valve 168 may be opened at the end of the breath-hold period. In Step 710, controller 220 may receive the imaging data (e.g. from the MRI RF system).

In Step 712, controller 220 may determine evaluation parameters based on output from sensors 230 and 240. In some embodiments, controller 220 may determine the evaluation parameters from the portions of the signals which were collected by sensors 230, 240 during the breath-hold period. In alternative embodiments, controller 220 may also use portions of the signals occurring before breath-hold start time 618 and/or occurring after breath-hold end time 620. For example, controller 220 may use portions of the detected respiration signal and the detected cardiovascular signal which begin a pre-determined length of time (e.g. 5 seconds) before start time 618 and which end a pre-determined length of time (e.g. 5 seconds) after end time 620. In this way, controller 220 may generate evaluation parameters which are associated with the patient's state during the breath-hold and, optionally, of the patient's state before and/or after the breath-hold.

Controller 220 may compare the generated evaluation parameters to the baseline evaluation parameters to determine if the measured signals are sufficiently similar to the baseline signals. For example, controller 220 may calculate one or more values reflecting the variability between the generated evaluation parameters and their corresponding baseline parameters, such as the range, mean, variance, standard deviation, and percent difference. If the variability value for one or more evaluation parameters is above a threshold (e.g. a 5% difference), controller 220 may determine that the measured signals are dissimilar from the baseline signals and may conclude that the patient's breath-holding is unreproducible. However, if controller 220 determines that the calculated variability for all evaluation parameters is below the threshold, then controller 220 may determine that the breath-holding is reproducible.

In Step 714 controller 220 may elect to discard the imaging data if it determines that breath-holding during the prior imaging cycle is unreproducible. However, if controller 220 determines that breath-holding was reproducible (that is, the calculated variability for all evaluation parameters was below the threshold), controller 220 may store the collected imaging data in a memory storage device, such as database 210. In Step 716, controller 220 may repeat imaging until a sufficient number of images is collected.

In Step 718, controller 220 may determine that a sufficient number of images are collected and may process the imaging data to generate a tumor model, such as a 4D tumor model. According to various embodiments, controller 220 may evaluate the received images to delineate a target, such as the target tumor, from surrounding healthy tissue. For example, controller 220 may contour the target tumor in each 2D or 3D image slice, and may combine them to generate a 4D model of the tumor. The contour may be generated automatically (e.g., using a program such as the Atlas-based auto-segmentation software, ABAS®, manufactured by Elekta AB of Stockholm, Sweden). One of ordinary skill in the art will appreciate that the tumor modeling process described herein is merely exemplary, and that any suitable modeling technique may be utilized to generate the tumor model from the received imaging data.

In Step 720, controller 220 may determine a correlation between tumor position and the subject's cardiovascular and respiratory signals. This determination may include identifying the exact location of the tumor during the breath-hold. In some embodiments, this determination may additionally include the determination of any slight tumor movement which may occur during the breath-hold. During the breath-hold, controller 220 may immobilize the tumor in approximately the same location because movement of the lungs and diaphragm is immobilized due to blocked airflow in ABC 160. This may be due, at least in part, to the fact that the position of some tumors, such as lung tumors, is based upon motion of the lungs and diaphragm. However, it is possible that the tumor may move a very small distance during the breath hold due to cardiac rhythm and bloodflow. These phenomena may be indicated by the cardiovascular signal. Thus, controller 220 may compare detected tumor movement with the received cardiovascular signal to determine a correlation therebetween. Tumor position and movement, as indicated by the cardiovascular and respiratory signals, may be built into the tumor model by controller 220, thus generating tumor model 215. As a result, position and movement of the tumor may be accurately predicted by detected cardiovascular and respiratory signals because their positional correlation is known and built into the tumor model.

In Step 722, controller 220 may generate radiotherapy treatment plan 216 based upon the tumor model. In some embodiments, the treatment plan may include radiation dose, as well as other parameters such as beam angles, dose-histogram-volume information, the number of radiation beams to be used during radiotherapy, the dose per beam, and the like. Factors such as the location and size of the target tumor may be taken into consideration to achieve a balance between efficient treatment of the tumor (e.g., such that the tumor receives enough radiation dose for an effective therapy) and low irradiation of the healthy surrounding tissue (e.g., the healthy surrounding tissue receives as low a radiation dose as possible). In some embodiments, controller 220 may determine a dose of radiation to be applied to the tumor, as well as any maximum amounts of dose that may be received by the healthy tissue surrounding the tumor (e.g., lung tissue, nervous tissue, cardiac tissue, and the like). One of ordinary skill in the art will appreciate that the treatment planning process described herein is merely exemplary, and that any suitable treatment planning process may be utilized according to the present disclosure. Controller 220 may output the tumor model and treatment plan to a suitable data storage site from which it may be accessed for subsequent evaluation and use, such as to database 210.

Figure 7B:
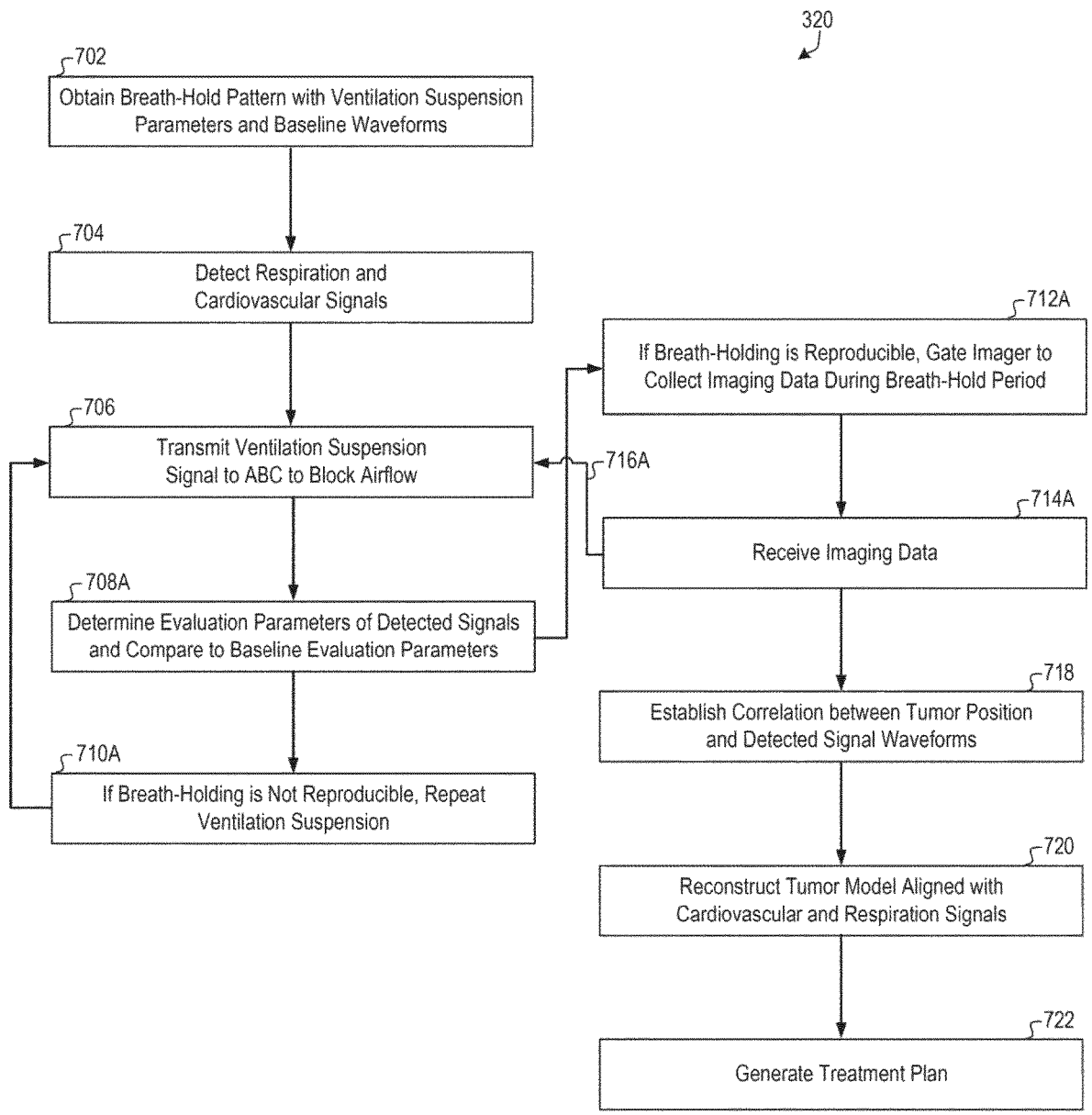
FIG. 7B illustrates a flow diagram of an alternative exemplary treatment planning session, according to various embodiments of the present disclosure.

FIG. 7B illustrates exemplary steps performed during a treatment planning session 320, according to various alternative embodiments (e.g., as an alternative to embodiments consistent with FIG. 7A). For example, exemplary steps illustrated in FIG. 7B may be executed by controller 220. After closure of valve 168 in Step 706, in Step 708A controller 220 may generate the evaluation parameters of the detected cardiovascular and respiratory signals and compare them to the baseline evaluation parameters to determine if breath-holding is reproducible. In Step 710A, if controller 220 determines that breath-holding is not reproducible, it may repeat ventilation suspension until it determines a reproducible breath-hold. However, in Step 712A, if controller 220 determines that breath-holding is reproducible, it may gate the imager of imaging device 140 to receive imaging data during the breath-hold period. Controller 220 may receive the imaging data in Step 714A and may proceed with Steps 718-722. Optionally, controller 220 may repeat imaging in Step 716A until a sufficient number of images are received. According to these alternative embodiments, rather than receiving imaging data and then evaluating breath-holding reproducibility, as in previous embodiments, controller 220 may instead evaluate reproducibility of the breath-holding before imaging begins. Should controller 220 determine that the breath-holding is sufficiently similar to baseline, it may control the imager to receive the imaging data.

Figure 8:
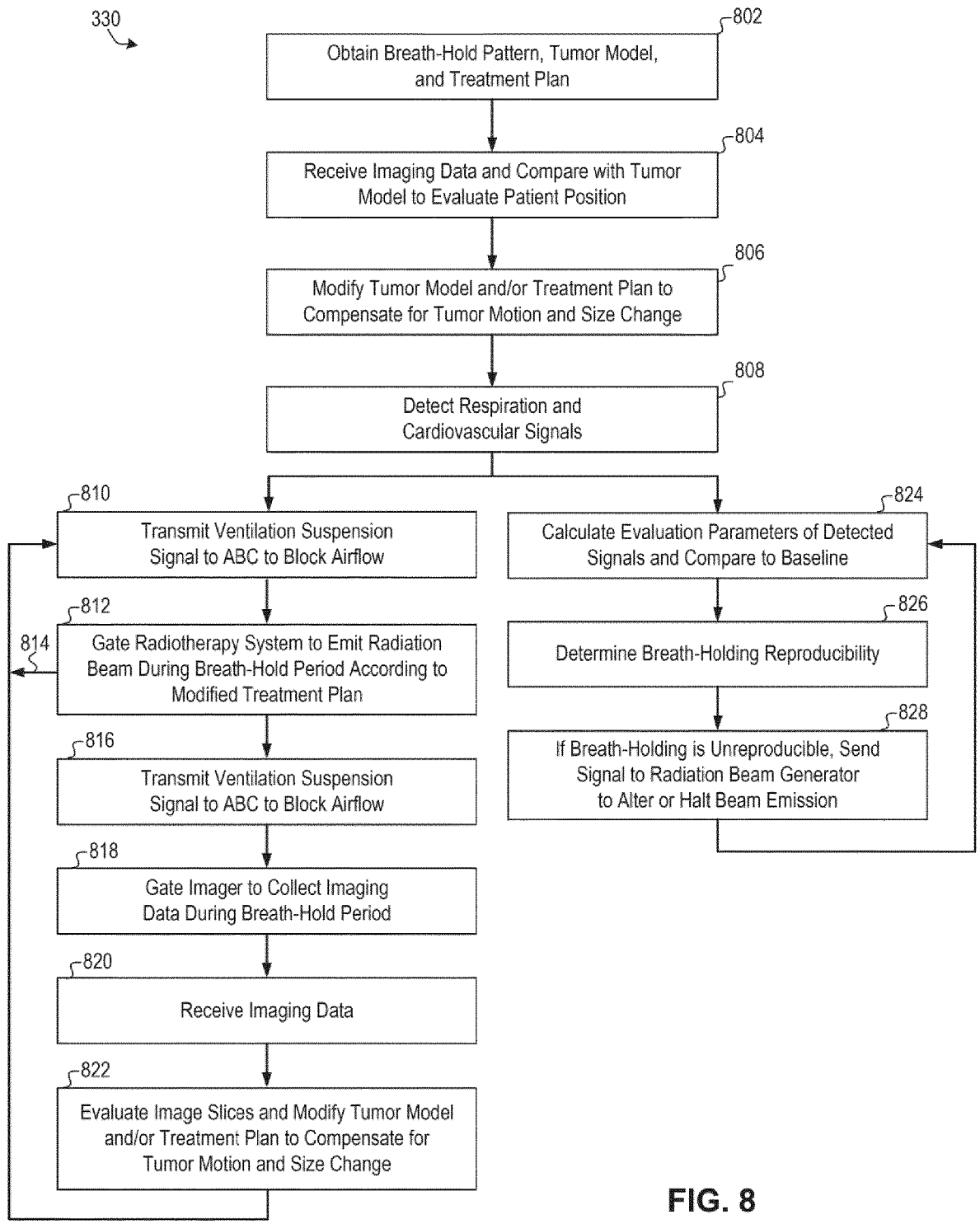
FIG. 8 illustrates a flow diagram of an exemplary treatment delivery session, according to various embodiments of the present disclosure.

FIG. 8 illustrates exemplary steps performed during a radiotherapy treatment session 330. In some embodiments, treatment session 330 may be executed by controller 220 to treat a target tumor. The target tumor may be treated according to the treatment plan generated during planning session 320. Output from sensors 230 and 240 may be utilized to monitor the patient's respiratory motion and the target tumor position because the correlation between tumor position and cardiovascular and respiratory signals has been established in Step 720 of the treatment planning session.

In Step 802, controller 220 may receive the patient's breath-hold pattern, including ventilation suspension parameters 211, baseline signals 212 and 213, and baseline evaluation parameters 214. Additionally, controller 220 may receive tumor model 215 and treatment plan 216. In some embodiments, controller 220 may receive this data from database 210. In Step 804, controller 220 may control imaging device 140 to collect imaging data from the patient, and may compare the imaging data to model 215 to evaluate the placement of the patient within the treatment area. For example, the patient may lie upon couch 180 in a slightly different position than during planning session 320. In some embodiments, controller 220 may control couch 180 to move along one or more axes until the patient is correctly position for treatment. In Step 806, controller 220 may modify one or more of tumor model 215 and treatment plan 216 according to the collected imaging data. For example, the target tumor may have moved, or changed in size or shape, between planning session 320 and treatment session 330. In some embodiments, such a modification may be performed by treatment planning module 222, which may modify model 215 and plan 216 using the imaging data to generate modified model 225 and modified plan 226. Thus, changes in tumor position and/or size may be accounted for.

In Step 808, controller 220 may receive output from sensors 230 and 240. Upon detection of the requisite portion of the patient's respiratory signal (e.g. end-exhalation), controller 220 may send a ventilation suspension signal to ABC 160 to close valve 168 for the requisite breath-hold period duration. During the breath-hold period, in Step 812 controller 220 may gate beam generator 124 to emit radiation to the target tumor. Controller 220 may also control beam generator 124 and beam shaping device 126 such that the delivered radiation beam corresponds to modified treatment plan 226. As illustrated by Arrow 814, after Step 812 controller 220 may repeat Steps 810 and 812 one or more times to irradiate the target tumor.

As explained further below in reference to Steps 824-828, during Steps 810 and 812, signals detected by sensors 230, 240 may be utilized by controller 220 to determine the position of the tumor, and to anticipate with high certainty future movement of the tumor. This is because the patient performs the established breath-hold pattern during radiotherapy, and because the tumor model includes a correlation between tumor location and the cardiovascular and respiratory signals which are associated with the breath-hold pattern. Thus, controller 220 may control radiotherapy device 120 to deliver the radiation beam to the tumor location indicated by the detected cardiovascular and respiratory signals. In some embodiments, a reduced number of images, or even no images, need be collected to monitor the patient during radiotherapy because the detected cardiovascular and respiratory signals may be evaluated to ensure that the patient is adequately performing the established breath-hold pattern and to determine the tumor position. Additionally, monitoring of the breath-hold by controller 220 may permit Steps 810 and 812 to be repeated a number of times without imaging (as indicated by 814) because the position of the tumor is known with high certainty.

During treatment session 330, controller 220 may occasionally receive images from imaging device 140 to evaluate changes to the tumor and/or to monitor the patient. Controller 220 may transmit a ventilation suspension signal to ABC 160 in Step 816, may gate the imager in 818, and may receive imaging data in step 820. In Step 822, controller 220 may process the imaging data to evaluate movement of the tumor, and/or changes in tumor size and shape. In some embodiments, controller 220 may further modify the treatment plan to compensate for any determined changes to the tumor. Controller 220 may additionally evaluate the imaging data to determine if the patient has moved during the previous course of radiotherapy, and may further reposition couch 180 if needed to realign the tumor with the radiation beam.

During radiotherapy, the detected cardiovascular and respiratory signals may be evaluated by controller 220 to ensure that the patient is performing the established breath-hold pattern with sufficient reproducibility. In Step 824, controller 220 may generate the evaluation parameters and compare them to baseline parameters, and in Step 826, controller 220 may calculate the variability between them to determine if breath-holding is reproducible. According to Step 828, if controller 220 determines that breath-holding is not reproducible (i.e. the calculated variability is equal to or greater than a pre-determined threshold, for example, a 5% difference), controller 220 may send a control signal to beam generator 124 to alter or cease radiation delivery. For example, the patient may become panicked or anxious during the radiotherapy session, which may cause their respiratory movements to become quick and unpredictable. Alternatively, the patient may become fatigued during radiotherapy and may be momentarily unable to sustain the breath-hold. By altering or halting radiation delivery, controller 220 may ensure that healthy tissue is not inadvertently irradiated by radiotherapy device 120. Controller 220 may continue monitoring output from sensors 230, 240 until the patient resumes reproducible breath-holding, after which radiotherapy may continue. However, if at Step 828 controller 220 determines that breath-holding is reproducible (i.e. the calculated variability is below the pre-determined threshold), controller 220 may proceed with Step 812 and gate the radiotherapy device to emit the radiation beam during a breath-hold period because the position of the tumor can be determined with high certainty. Controller 220 may continuously perform Steps 824-828 during treatment session 330.

Figure 9:
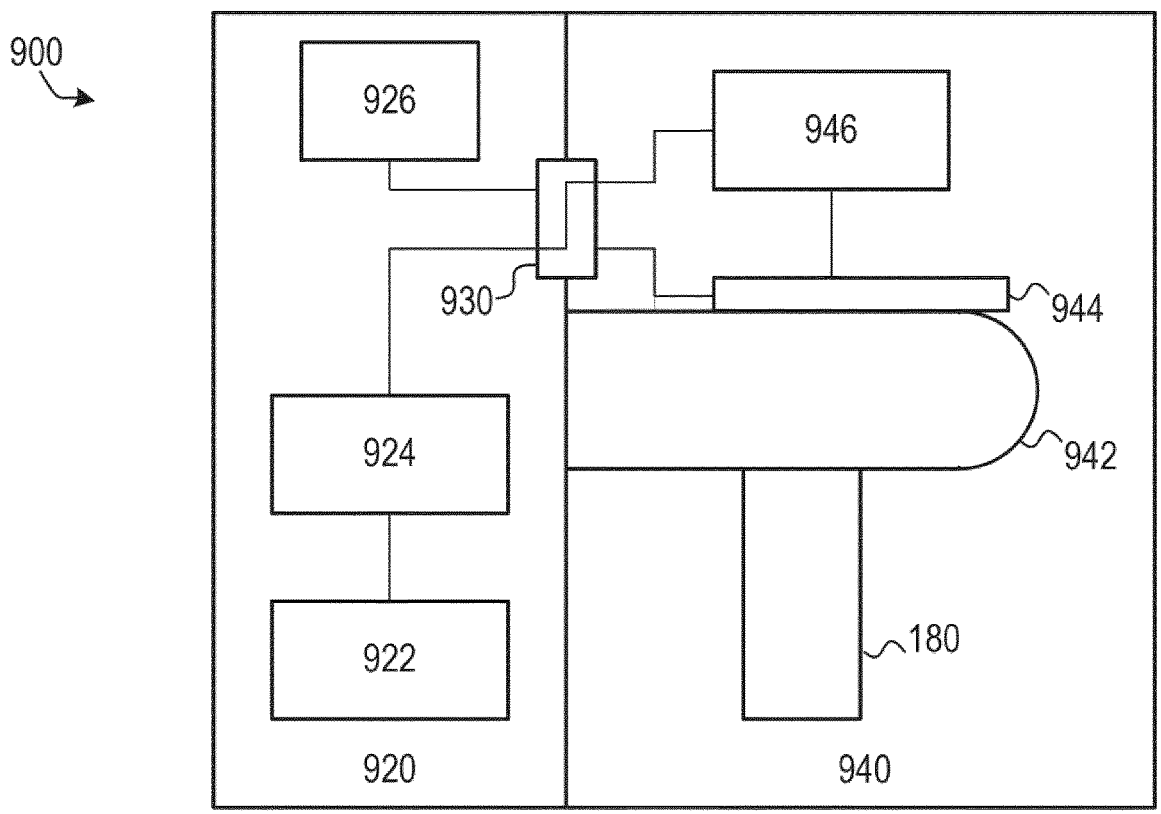
FIG. 9 illustrates a diagram of an exemplary MR-compatible radiotherapy environment, according to various embodiments of the present disclosure.

FIG. 9 illustrates a diagram of an exemplary MR-compatible radiotherapy environment 900, according to various embodiments of the present disclosure. Radiotherapy environment 900 may include a technical room 920 and an examination room 940, which may be RF-shielded. Within examination room 940, a treatment housing 942 may include radiotherapy device 120 and imaging device 140, with couch 180 arranged therein. An accessory housing 944 may include, for example, ABC 160, cardiovascular sensor 230, and respiration sensor 240. A gating module 922 may be arranged within technical room 920, the gating module 922 configured to send gating signals from controller 220 to radiotherapy device 120 and imaging device 140.

To reduce electronic noise and to avoid artifacts associated with imaging (e.g. MRI artifacts), environment 900 may utilize optical fiber to connect the various components therein. Optical converters 924 and 946 may be utilized in each room, for example to convert optical signals transmitted between gating module 922 and components within housings 942 and 944. Alternatively or additionally, environment 900 may utilize Wi-Fi to connect the various components therein. For example, the Wi-Fi may be configured according to IEEE 802.11 specifications, with a minimum frequency of 2.4 GHz so as to avoid generation of imaging artifacts. Housings 942 and 944 may be shielded against interfering noise and artifacts. Further, a power supply 926 for powering the components within examination room 940 may pass power lines through a shielded filter box 930. In some embodiments, an existing headset within examination room 940 may be utilized to output audio guidance or relaxing sounds or music to the patient. Alternatively or additionally, to avoid generation of noise with a display device, visual feedback may be projected upon a wall of examination room 940 and/or within the bore of system 100 to provide signal feedback to the patient, with the use of a mirror to output readout.

Figure 10:
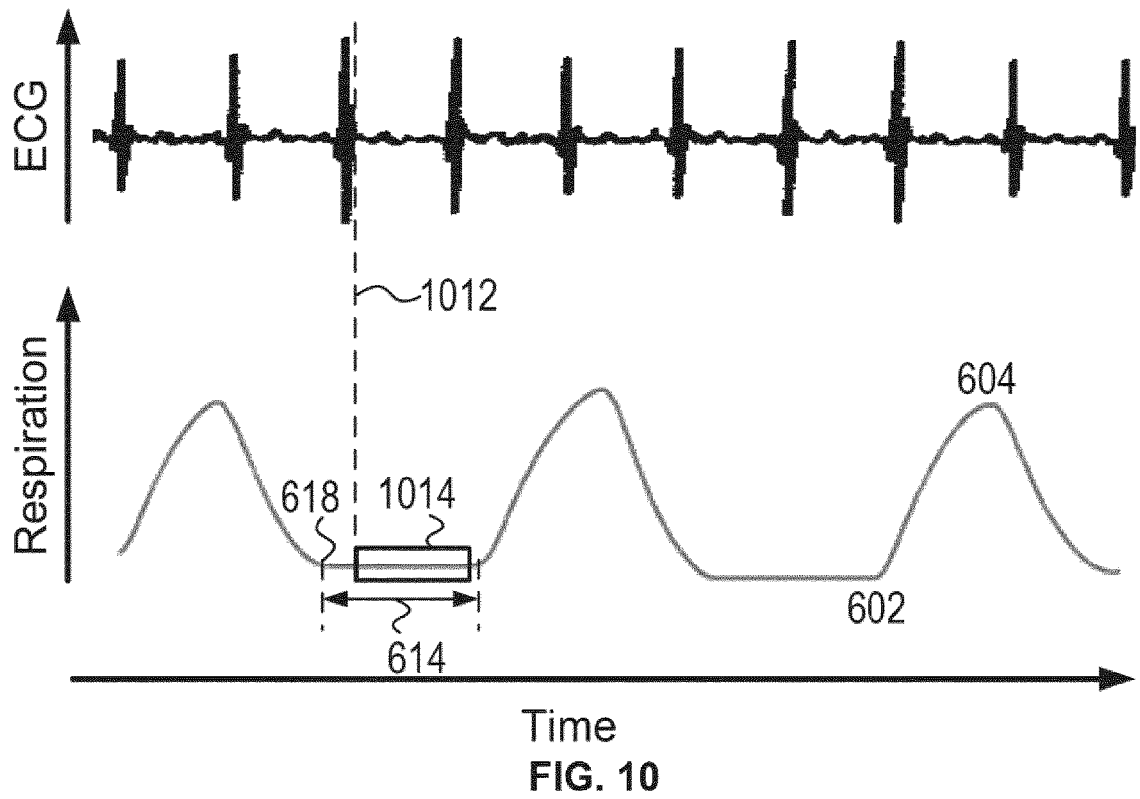
FIG. 10 illustrates exemplary respiratory and ECG signals during ECG-triggered imaging or radiotherapy, according to various embodiments of the present disclosure.

FIG. 10 illustrates an exemplary ECG-triggering technique. The technique of FIG. 10 may be executed by a processor such as controller 220 and may optionally be performed during imaging and/or radiotherapy to reduce artifacts from blood flow and heart movement. According to the technique of FIG. 10, a breath-hold period may be triggered according to methods described above, for example by monitoring of the patient's respiration cycle and/or by scanning the patient's diaphragm and/or lungs with a navigator channel (or another fast-acquisition output) of an imaging device (e.g. imaging device 140). During the breath-hold period, controller 220 may monitor the detected cardiovascular signal to identify one or more phenomena therein, and may generate a gating signal 1012 upon detection thereof. A window 1014 may begin upon generation of gating signal 1012 and may last for a duration ranging from milliseconds to several seconds. According to embodiments in which the technique of FIG. 10 is performed during imaging, such as with imaging device 140, the imager may be gated by controller 220 to only collect images during a window 1014. Similarly, according to embodiments in which the technique of FIG. 10 is performed during radiotherapy, such as with radiotherapy device 120, controller 220 may gate beam generator 124 to only generate radiation during a window 1014.

The embodiment illustrated in FIG. 10 illustrates a cardiovascular signal which includes an ECG signal; additionally or alternatively, an $SpO_2$ signal may be used. According to embodiments including use of an ECG signal, controller 220 may monitor the ECG signal for the occurrence of diastole, at which time the controller 220 may generate a gating signal 1012. In some embodiments, controller 220 may detect one or more phenomena in the ECG signal to determine the beginning of diastole, such as the S-wave or the T-wave. Alternatively or additionally, controller 220 may detect the R-wave and may generate gating signal 1012 after a pre-determined length of time, such as 200 milliseconds. Window 1014 may begin at gating signal 1012, and may last for a duration of time ranging from milliseconds to several seconds. For example, controller 220 may control window 1014 to last for a duration of between 200 and 500 milliseconds. In some embodiments, controller 220 may receive ECG data from the patient prior to imaging and/or radiotherapy, and may process the ECG signal to select a duration of window 1014 for the patient. For example, controller 220 may analyze the patient's ECG signal to determine the duration of, for example, the S-Q segment, the T-Q segment, the S-R segment, and/or the T-R segment, and may adjust the duration of window 1014 to correspond to one or more of the determined segment durations. In some alternative embodiments, controller 220 may gate window 1014 to end upon detection of a P-wave within the ECG signal. Window 1014 may have a duration shorter than breath-hold period duration 614, so as to ensure that window 1014 occurs during a period in which both the respiratory anatomy and the heart are motionless. In some embodiments, controller 220 may gate window 1014 to end upon detection of breath-hold end time 620, such as in the event that end time 620 is detected by controller 220 prior to the end of window 1014.

Imaging and/or radiotherapy may be performed during window 1014, in which time the patient's respiratory and cardiovascular anatomy are motionless during diastole. Thus, images collected during window 1014 may be free of artifacts caused by respiratory or cardiovascular activity. Further, radiation delivered during window 1014 may be more accurately aimed because the patient's anatomy is still, and because a treatment plan generated from images collected during a prior window 1014 may be highly accurate. The technique depicted in FIG. 10 may be repeated one or more times, for example until a required number of images are collected or until a radiotherapy treatment session is completed.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may include a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the invention.

Embodiments may be implemented with computer-executable instructions. The computer-executable instructions may be organized into one or more computer-executable components or modules. Embodiments may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a," "an," and "the" are intended to mean that there are one or more of the elements. The terms "comprising," "including," and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The invention claimed is:

1. A radiotherapy device for emitting a radiation beam to treat a target tumor of a patient, wherein the radiotherapy device is configured to communicate with a breath control device for controlling breathing by the patient during radiotherapy of the target tumor, the breath control device comprising a selectively-operable valve, the radiotherapy device comprising:
   a radiation beam generator for emitting the radiation beam toward the target tumor; and
   a controller configured to:
   obtain a pre-determined breath-holding pattern for the breath control device, the breath-holding pattern including:
   at least one ventilation suspension parameter for the breath control device;
   a baseline respiration signal corresponding to the at least one ventilation suspension parameter; and
   a baseline cardiovascular signal corresponding to the at least one ventilation suspension parameter;
   detect a respiration signal reflecting respiration of the patient;
   detect a cardiovascular signal reflecting cardiovascular activity of the patient;
   transmit ventilation suspension signals to the breath control device to control the valve of the breath control device to block airflow to the patient during corresponding breath-hold periods included in the breath-holding pattern, wherein the ventilation suspension signals are based upon the at least one ventilation suspension parameter;
   calculate a variation between the detected respiration and cardiovascular signals and the obtained baseline respiration and cardiovascular signals; and
   determine, when the calculated variation is below a pre-determined threshold, to gate the radiation beam generator, such that the radiation beam generator is gated to emit the radiation beam during one or more of the breath-hold periods and when the calculated variation is below the pre-determined threshold.

2. The radiotherapy device in accordance with claim 1, wherein the at least one ventilation suspension parameter is obtained during a training period and includes a breath-hold period duration and a start time of each breath-hold period, the start time being one or more of an end-exhalation and an end-inhalation.

3. The radiotherapy device in accordance with claim 1, wherein the radiation beam generator is configured to emit the radiation beam according to a treatment plan corresponding to the at least one ventilation suspension parameter, the baseline respiration signal, and the baseline cardiovascular signal.

4. The radiotherapy device in accordance with claim 3, further comprising an MR imaging device used to acquire MR image data of the target tumor,
wherein the controller is further configured to:
receive imaging data from the imaging device;
determine, from the imaging data, one or more of movement and a size change of the target tumor; and
modify the treatment plan according to the one or more of determined movement and size change of the target tumor.

5. The radiotherapy device in accordance with claim 1, wherein the cardiovascular signal is one or more of an ECG signal and a pulse oximetry signal.

6. The radiotherapy device in accordance with claim 1, wherein the calculated variation reflects one or more parameters associated with at least one of inhalation rising time, exhalation falling time, breath-hold period duration, respiration cycle duration, respiration signal amplitude, cardiovascular cycle duration, and cardiovascular signal amplitude.

7. The radiotherapy device in accordance with claim 1, wherein the controller is further configured to determine, from the detected cardiovascular signal, a cardiovascular cycle duration representing a time period between two consecutive heartbeats, wherein the calculated variation reflects a comparison between the detected respiration signal and the cardiovascular cycle duration.

8. The radiotherapy device in accordance with claim 1, wherein the controller is further configured to predict one or more of location and movement of the target tumor based upon the detected signals.

9. The radiotherapy device in accordance with claim 1, wherein when the calculated variation is equal to or greater than the pre-determined threshold, the controller is further configured to halt emission of the radiation beam by the radiation beam generator.

10. The radiotherapy device in accordance with claim 1, wherein the controller is further configured to:
determine a plurality of diastole time periods based on the detected cardiovascular signal; and
determine a plurality of radiotherapy activation periods based on the occurrence of both one of the breath-hold periods and one of the diastole time periods;
wherein determining to gate the radiotherapy device further comprises gating the radiotherapy device such that the radiotherapy device emits the radiation beam only during one or more of the plurality of radiotherapy activation periods.

* * * * *